(12) United States Patent
Lorito et al.

(10) Patent No.: US 10,875,898 B2
(45) Date of Patent: Dec. 29, 2020

(54) BIOACTIVE PROTEIN, USE THEREOF AND METHOD FOR ITS PRODUCTION

(71) Applicant: Koppert B.V., Berkel en Rodenrijs (NL)

(72) Inventors: Matteo Lorito, Salerno (IT); Michelina Ruocco, Naples (IT); Francesco Vinale, Naples (IT); Sheridan Lois Woo, Salerno (IT)

(73) Assignee: Koppert B.V., Berkel en Rodenrijs (NL)

( * ) Notice: Subject to any disclaimer, the term of this patent is extended or adjusted under 35 U.S.C. 154(b) by 0 days.

(21) Appl. No.: 16/297,120

(22) Filed: Mar. 8, 2019

(65) Prior Publication Data
US 2020/0031882 A1 Jan. 30, 2020

Related U.S. Application Data

(63) Continuation of application No. 15/120,456, filed as application No. PCT/NL2015/050115 on Feb. 23, 2015, now abandoned.

(30) Foreign Application Priority Data

Feb. 21, 2014 (EP) .................................... 14156146
Dec. 10, 2014 (EP) .................................... 14197253

(51) Int. Cl.
*C07K 14/37* (2006.01)
*A01N 63/30* (2020.01)
*A01H 5/10* (2018.01)

(52) U.S. Cl.
CPC .............. *C07K 14/37* (2013.01); *A01H 5/10* (2013.01); *A01N 63/30* (2020.01)

(58) Field of Classification Search
None
See application file for complete search history.

(56) References Cited

U.S. PATENT DOCUMENTS 8,822,190 B2 * 9/2014 Reddy ..................... C05F 11/08
435/174

FOREIGN PATENT DOCUMENTS

| CN | 1337459 A | 2/2002 |
|---|---|---|
| CN | 102212485 B | 12/2012 |
| WO | WO2009091557 A1 | 7/2009 |
| WO | WO2010091337 A1 | 8/2010 |
| WO | WO2013149801 A1 | 10/2013 |

OTHER PUBLICATIONS

Ruocco et al. Accession No. A3RJX1, deposited 2007.*
Ruocco et al. Accession No. EF419429, deposited 2007.*
Ruocco et al. MPMI (2015), vol. 28 (2): 167-179.*
Nigro, Effect of Metabolites Produced by Beneficial Fungi on the Plant Metabolome, Physiology and Agronomic Performance, Apr. 3, 2013, XP055186100, Italy, Retrieved from the Internet: URL:http://catalog.hathitrust.org/Record/007929804 [retrieved on Apr. 27, 2015] the whole document.
Subname: Full=Class II hydrophobin; Flags: Fragment, UNIPROT, Apr. 3, 2007, XP002727458, [retrieved on Apr. 3, 2007] sequence.
Battaglia et al., Tomato Below Ground—Above Ground Interactions: Trichoderma longibrachiatum Affects the Performance of Macrosiphum euphorbiae and Its Natural Antagonists, Oct. 2013, vol. 26, No. 10 pp. 1249-1256.
Hermosa et al., Plant-beneficial effects of Trichoderma and of its genes, Microbiology, Jan. 1, 2012, Microbiology 158: 17-25.
Vinale et al., Harzianic acid: a novel siderophore from Trichoderma harzianum, FEMS Microbiol Lett. Sep. 10, 2013; 347(2):123-9.
Harman et al., Changing Paradigms on the Mode of Action and Uses of *Trichoderma* spp. for Biocontrol, Outlooks on Pest Management 19(1):24-29, Feb. 2008.
Lorito et al., Translational research on Trichoderma: from 'omics to the field, Annu Rev Phytopathol. 2010;48:395-417.
Sanchez et al., In vitro antagonism of Thielaviopsis paradoxa by Trichoderma longibrachiatum, Mycopathologia. Jan. 2007;163(1):49-58.
Ruocco et al., Hytral from the beneficial fungus Trichoderma harzianum T22 is an elicitor of defence response in plant, Internet Citation, Jan. 1, 2007, XP007922780, Retrieved from the Internet: URL:http://wiki.pestinfo.org/wiki/Journal_of_Plant_Pathology_%282007%29_89,_p._S21_%28Ruocco_et_al.%29 [retrieved on Jul. 15, 2014].
Hoyos-Carvajal et al., Growth stimulation in bean (*Phaseolus vulgaris* L.) by Trichoderma, Biological Control vol. 51, Issue 3, Dec. 2009, pp. 409-416.
Freitas et al., Cloning and characterization of a protein elicitor Sm1 gene from Trichoderma harzianum, Biotechnol Lett (2013) 36(4): 783-788.

* cited by examiner

*Primary Examiner* — Medina A Ibrahim
(74) *Attorney, Agent, or Firm* — Bret E. Field; Bozicevic, Field & Francis LLP

(57) ABSTRACT

The present invention according to a first aspect relates to a *Trichoderma longibrachiatum* strain comprising an autologous nucleotide sequence coding for a protein having at least 70% sequence similarity with the amino acid sequence of SEQ ID NO: 1 and its use for the treatment of a plant. Further aspects of the invention relate to a protein derived from said strain, methods for producing the protein, the use of the protein for the treatment of a plant and compositions comprising a source of the protein of the invention. Yet Further aspects of the invention relate to seeds treated with a source of the protein and methods for growing plants incorporating the step of treating said plants with the composition of the invention.

16 Claims, 16 Drawing Sheets
Specification includes a Sequence Listing.

| A | % INCR VS. WATER | % INCR VS. Commercial product | % INCR VS. T22 |
|---|---|---|---|
| Root length | +38,4 | +57,3 | +23,7 |
| Plant height | +16,5 | +43,8 | +12,4 |
| Root Fresh weight | +41,1 | +12,4 | +4,7 |
| Stem Fresh weight | +30,6 | +66,5 | +14,3 |
| Root Dry weight | +31,3 | +31,3 | +28,1 |
| Stem Dry weight | +18,4 | +49,0 | +17,3 |

BIOACTIVE PROTEIN, USE THEREOF AND METHOD FOR ITS PRODUCTION

FIELD OF THE INVENTION

The present invention relates to the field of agronomy. More in particular the invention relates to the stimulation and promotion of plant growth and/or plant health via the use of certain bioactive peptides alone and/or in combination with phytostimulants. According to certain aspects of the invention the promotion of plant growth and/or plant health is mediated by facilitating the interaction between the plant and plant stimulatory fungal species, such as *Trichoderma* spp.

STATE OF THE ART

Fungi belonging to the genus *Trichoderma* are more and more subject of study, both because of their relevance as pathogen antagonists and their active and positive interaction with the colonized plants. Thanks to these beneficial characteristics, bio-pesticides and bio-fertilizer that use *Trichoderma* spp. as active ingredient are developed and commercialized (Harman et al., 2010, Plant Disease 94:928-939).

*Trichoderma* antagonistic activity is principally based on mycoparasitism (Lorito et al., 1993, Phytopathology, 83:313-318; Lorito et al., 1996, Molecular Plant-Microbe Interactions, 9:206-213; Sanz et al., 2004, Current Genetics, 46: 277-286; Zeilinger et al., 1999, Fungal Genetics and Biology, 26:131-140), antibiosis (Schirmbock et al., 1994, Applied and Environmental Microbiology, 60:4364-4370; Vinale et al., 2008, Physiological and Molecular Plant Pathology, 72: 80-86, Vinale et al., 2009, Letters in Applied Microbiology, 48, 705-711) and competition for nutrients and ecological niches (Vargas et al., 2009, Plant Physiology, 151: 792-808). The mechanisms that regulate these processes are well known and widely studied. However, more recent information suggests that, in many cases, mycoparasitism and antibiosis are not the primary and unique mechanisms of biocontrol. In the last few years, study on induction of systemic plant resistance (TSR) by *Trichoderma* spp. during the biocontrol process had a growing importance and thus has been deeply explored (Yedidia et al., 1999, Applied and Environmental Microbiology, 65:1061-70; Woo et al., 2006, Phytopathology, 96:181-185; Shoresh et al., 2010, Phytopathology, 95:76-84; Harman et al., 2004, Nature Review Microbiology, 2: 43-56). Recent studies reported that some *Trichoderma* strains can activate ISR (Hanson and Howell 2004, Phytopathology, 94:171-176; Mandal and Mitra, 2007, Physiological and Molecular Plant Pathology, 71: 201-209; Segarra et al. 2007, Proteomics, 7:3943-3952), a mechanism triggered upon root colonisation by non-pathogenic rhizobacteria or fungi and regulated by a specific signal transduction cascade (Pieterse et al., 1996, Plant Cell, 8:1225-1237; Segarra, et al., 2009, Plant Biology, 11:90-96). In addition, plants whose roots are colonized by selected *Trichoderma* isolates are "sensitized" and respond faster and/or more intensely to pathogen attack, following a mechanism known as priming (Ahn, et al., 2007, Molecular Plant Pathogen Interaction, 20-759-768; Conrath et al., 2006, Plant Signalling and Behavior, 1:179-184).

More in general, a broad communication takes place between plants and microbes during the early stages of their association, in which signalling molecules play a crucial role. Unfortunately, the actors of the molecular cross-talk between *Trichoderma* spp. and the plants, that have been fully characterized since now with their role conclusively determined, are still few (Mukerjiee et al., 2013, *Trichoderma* Biology and Application, Stylus Pub Llc, London UK, 327 pp.)

In order to investigate whether any interesting signalling molecules relevant for the plant-microbe communication could be isolated from *Trichoderma* spp., the inventors of the present invention carried out experiments wherein the presence of Microbial Associated Molecular Patters proteins (MAMPs) produced by selected *Trichoderma* spp. during their interaction with plant material was investigated. Instead of selecting the *Trichoderma* species *T. harzianum, T. atroviride, T. asperellum, T. virens* most commonly applied in bio-pesticides and bio-fertilizer, the inventors of the present invention investigated a newly isolated strain of *T. longibrachiatum* (*T. longibrachiatum* strain MK1 (KV966), hereafter also indicated as MK1 or KV966. *T. longibrachiatum* strains in the field in general are not considered to be good candidate biocontrol agents. This is amongst others due to their unfavourable growth dynamics, but also because of their ability, not found in most other *Trichoderma* species, to grow at 37° C. Therefore, they have been much less investigated, from a molecular point of view, for biocontrol application purposes.

From *T. longibrachiatum* MK1 incubations, an about 7 KDa protein was selected for further analysis. This protein turned out to be a Type II hydrophobin protein and thus was designated HYTLO1. Subsequent experiments revealed surprising features of this protein from *Trichoderma longibrachiatum*, including plant growth modulation, including improvement of plant fresh weight, improvement of plant dry weight, improvement of root development, including improvement of root nodulation in Leguminosae, increase of germination percentage and increase of germination speed, disease and/or pathogen control and induction of systemic resistance. Autologous proteins from *Trichoderma* species, in particular *T. longibrachiatum*, having such features have not been described in the prior art.

SUMMARY OF THE INVENTION

The present invention thus according to a first aspect relates to the use of *Trichoderma longibrachiatum*, for the treatment of a plant, wherein the treatment of the plant preferably is aimed at one or more selected from (a) plant growth modulation, such as improvement of plant fresh weight, improvement of plant dry weight, improvement of root development, including improvement of root nodulation in Leguminosae, increase of germination percentage and/or increase of germination speed, or (b) disease control, such as via anti-microbial activity, preferably antifungal activity, or via stimulation of systemic resistance. According to certain embodiments in the use, the *Trichoderma longibrachiatum* may be combined with the use of one or more plant biostimulants selected from (i) a *Trichoderma* species other than *Trichoderma longibrachiatum*, (ii) harzianic acid or a biologically active isomer thereof, such as iso-harzianic acid, (iii) 6-pentyl-α-pyrone or (iv) *Rhizobia*.

A further aspect of the invention relates to a composition comprising a protein having at least 70% sequence similarity with an amino acid sequence according to SEQ ID NO: 1, characterized in that the protein is obtained as an autologous protein from *Trichoderma longibrachiatum* wherein in said composition the protein preferably is in a purified form. According to certain embodiments, in the composition the protein may be combined with one or more plant stimulants, such as selected from (i) a *Trichoderma* species, preferably a *Trichoderma* species other than *Trichoderma longibrachiatum*, (ii) harzianic acid, or a biologically active isomer thereof, such as iso-harzianic acid or (iii) 6-pentyl-α-pyrone.

Yet another aspect of the invention relates to the use of a protein having at least 70% sequence similarity with an amino acid sequence according to SEQ ID NO: 1, for the treatment of a plant, characterized in that the protein is provided as an autologous protein from *Trichoderma longibrachiatum*. In said use the treatment of the plant may be aimed at one or more selected from (a) plant growth modulation, such as improvement of plant fresh weight, improvement of plant dry weight, improvement of root development, including improvement of root nodulation in Leguminosae, increase of germination percentage and/or increase of germination speed, or (b) disease control, such as via antimicrobial activity, preferably antifungal activity, or via stimulation of systemic resistance. According to certain embodiments in this use, the protein may be combined with the use of one or more plant biostimulants selected from (i) a *Trichoderma* species, preferably a *Trichoderma* species other than *Trichoderma longibrachiatum*, (ii) harzianic acid, or a biologically active isomer thereof, such as iso-harzianic acid, (iii) 6-pentyl-α-pyrone or (iv) *Rhizobia*.

Further aspects of the invention relate to a method for producing a protein having at least 70% sequence similarity with an amino acid sequence according to SEQ ID NO: 1 and the protein obtainable with this method. The method comprises:

providing a strain of *Trichoderma longibrachiatum* comprising a functional autologous gene coding for the protein;

culturing biomass of the *Trichoderma longibrachiatum* strain under conditions suitable for expression of the gene;

obtaining the protein from the cultured biomass.

The *Trichoderma longibrachiatum* strain MK1 (KV966) is yet a further aspect of the invention. This strain is suitable for application in the uses and methods of the invention. It has been deposited under the Budapest treaty with the Centraalbureau voor Schimmelcultures (CBS), Utrecht, the Netherlands, on Dec. 10, 2013 under deposit number CBS 137023.

FIG. 7: Effect of purified HYTLO1 on the activation of tomato plant defense responses. Leaves were injected with HYTLO1 at the indicated concentrations and analyzed after 48 hours by Real Time PCR for the accumulation of PR (Pathogenesis-Related)-proteins PR1, PR2 and PIN2 RNA (for methods see Tucci M., et al., 2011, Molecular Plant Pathology, 12:341-354) Values indicated the n. of fold increase vs. untreated control.

FIG. 8: Effect of purified HYTLO1 application on the infection of tomato leaves by the pathogen *B. cinerea.* 10 μL of a solution of HYTLO1 were applied to tomato leaves and 2 hours later 10 μL of a *B. cinerea* spore suspension $1\times10^6$/ml were applied on the same spot. The measures were taken 72 hours post inoculation. The standard deviation bars were obtained from at least three different experiments, with five replicates and a total of 15 treated leaves per treatment.

FIG. 9: Effect of purified HYTLO1 application on tomato plant and root development. Tomato roots (left) and tomato cuttings (right) were dipped in a HYTLO1 solution of 0.018 μM.

FIG. 10: Effect of HYTLO1 on tomato plant growth as compared to treatment with *T. harzianum* strain T22 or the Commercial product GERMON E (G-E) base on the auxin 1-naphthaleneacetic acid, commercialized by L. Gobbi, Italy. (A) Growth increase of root and stem of HYTLO1 vs. water control, GERMON E or T22, 10 days after treatment. (B) Increase of root development (HYTLO1 treatment on the left, untreated control on the right), (C) Effect of HYTLO1 on plant size compared to T22. (D) Effect of HYTLO1 on root development compared to water control, T22, GERMON E (also in combination with HYTLO1). HYTLO1 was applied at final concentration in the soil at $10^{-8}$ M.

Figure 11:
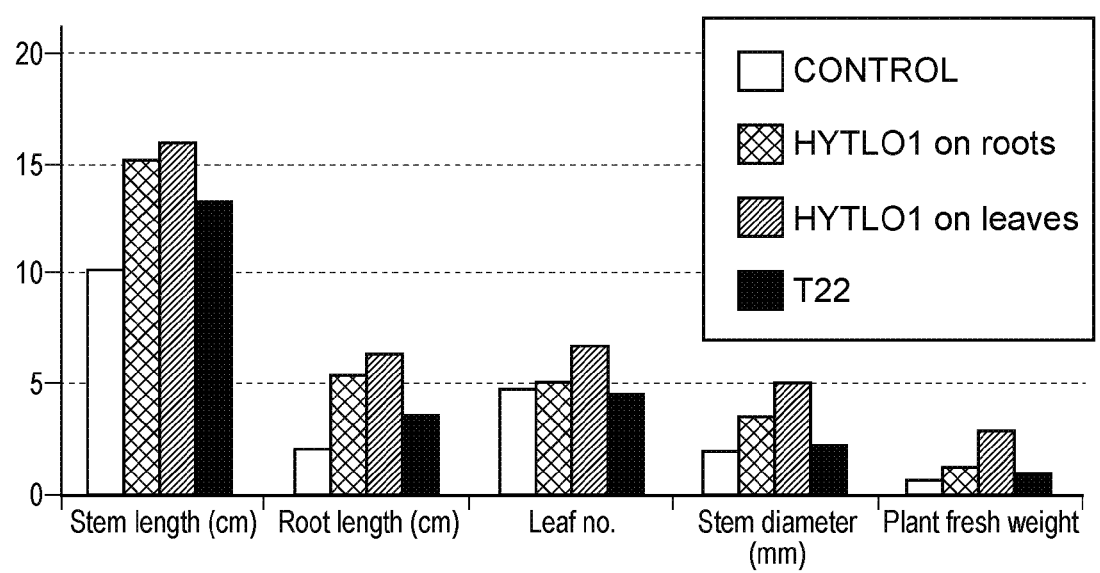

FIG. 11: Effect of purified HYTLO1 on tomato plants, applied by drench on the roots or by spraying on the leaves. For the irrigation, 50 ml of a solution containing 0.072 µg/ml of HYTLO1 (0.01 µM) were applied for each pot containing 1 litre of soil and 2 tomato plants, for a total of 4 applications. For foliar application, 20 ml of a solution containing 0.072 µg/ml (0.01 µM) of HYTLO1 were sprayed for each pot containing 2 tomato plants for a total of 4 applications.

Figure 12:
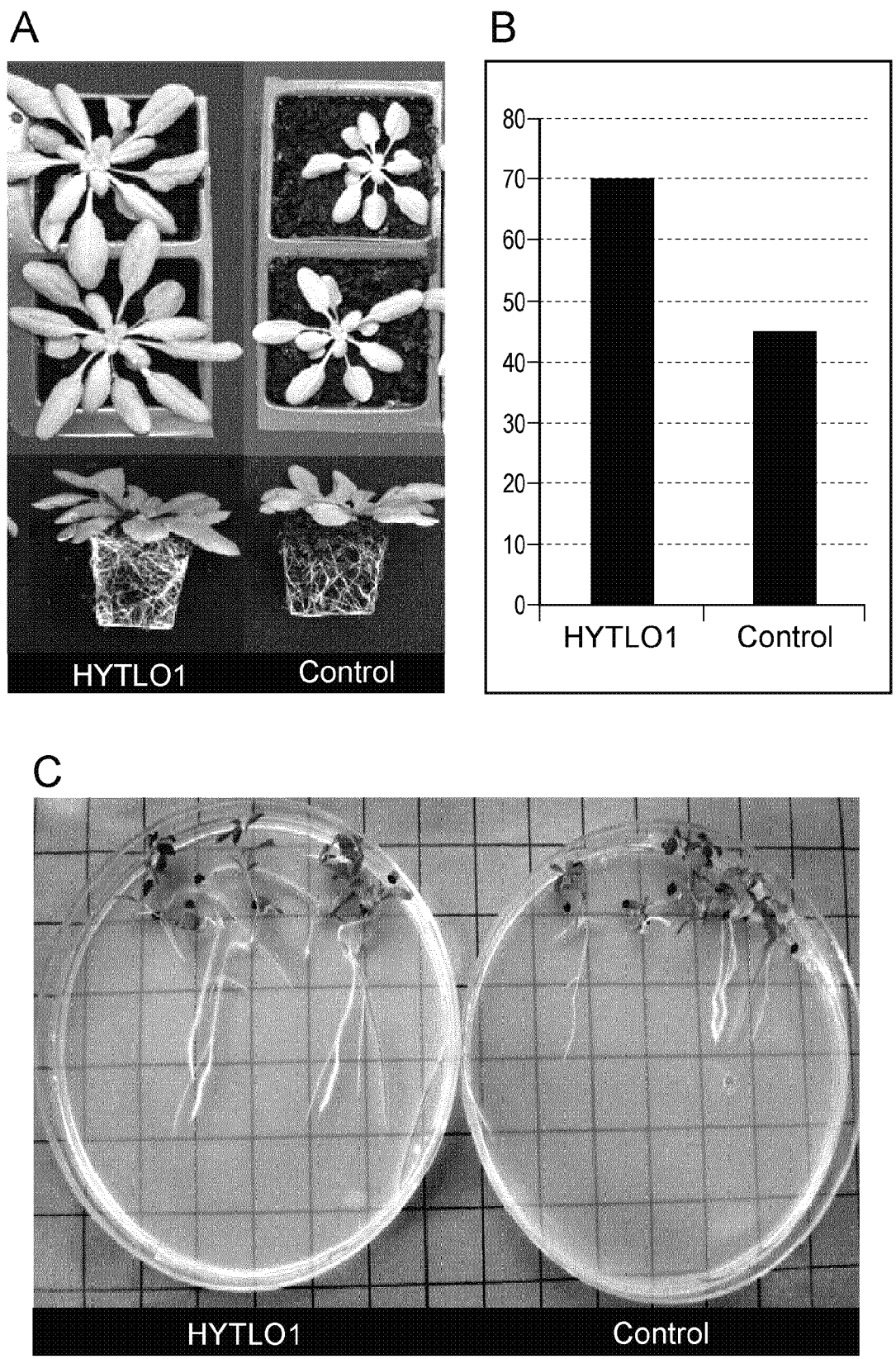

FIG. 12: Effect of purified HYTLO1 on the growth of *Arabidopsis* (A), percentage seed germination of cucumber (B) and plantlet development of *Lotus japonicus* (C). A: *Arabidopsis thaliana* (Columbia-0: Col-0) seeds were sown in Levington's F2 compost plus sand (JFC Munro, Devon; http://www.jfcmonro.com) and chilled for 2 days at 4° C. Plants were grown under short-day conditions (10 h light) in a controlled environment chamber, at 22° C. during the day and 18° C. at night with 60% relative humidity for 5-6 weeks before transplanting. Ten ml of sterile solutions of HYTLO1 were drenched every two days at concentrations 0.072 µg/ml (0.01 µM) for one month in each pot containing 100 ml of soil and 1 *Arabidopsis* plant. Untreated plants were used as controls. B: Sterile cucumber seeds were placed on magenta box containing half-strength Murashige and Skoog salt (MS) medium (ICN Biomedicals) containing 1% agar and 1.5% sucrose, adjusted to pH 5.7, and vernalized for 2 days at 4° C. in the absence of light. A sterile solutions of HYTLO1 was added to the substrate at final concentration of $10^{-8}$ M before the solidification of agar. C: The same concentration of HYTLO1 was used in the agarized medium used for the *L. japonicus* test.

Figure 13:
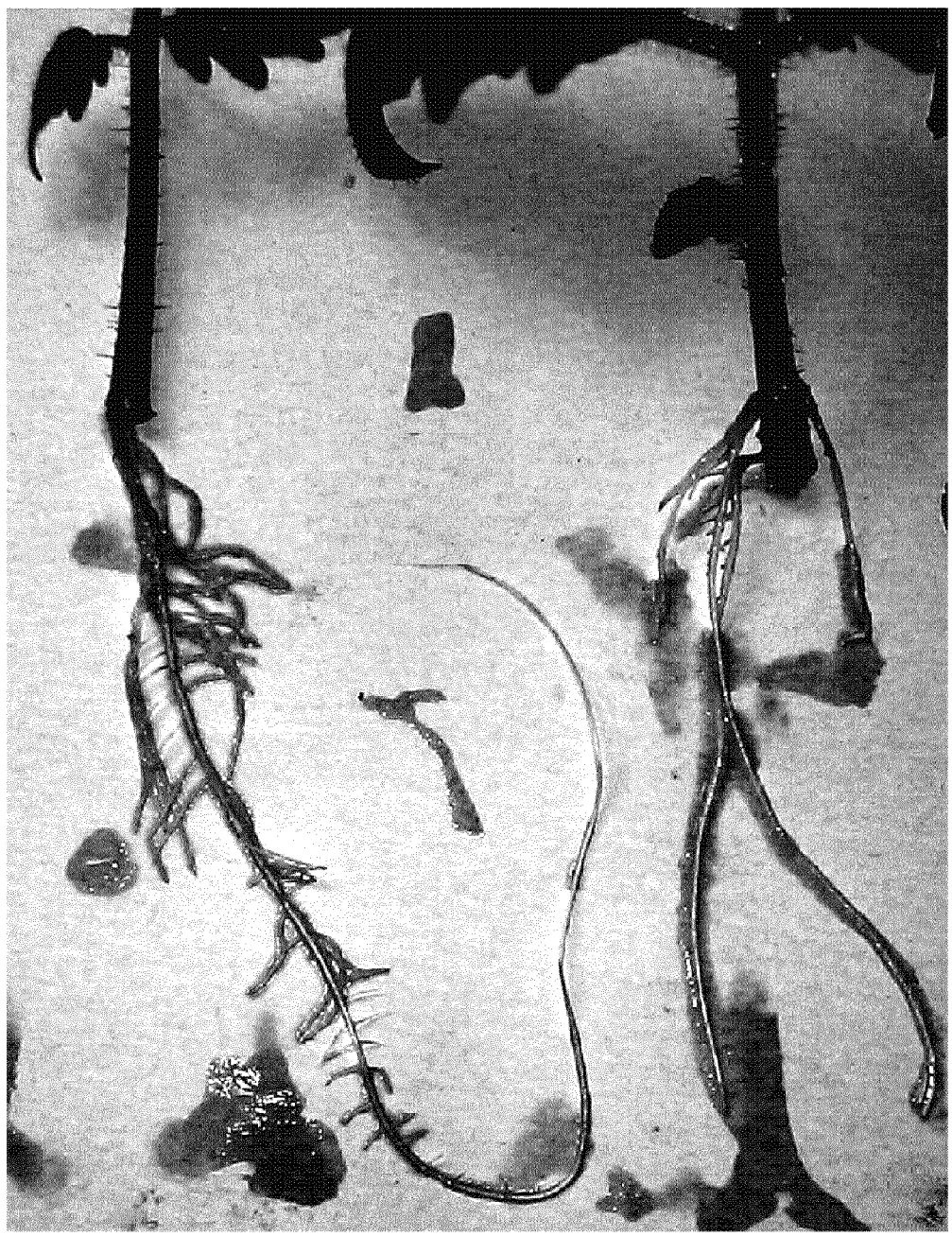

FIG. 13: Effect of transgenic expression of the Hytlo1 gene on tomato. Cuttings quickly form new roots in the presence of water.

Figure 14:
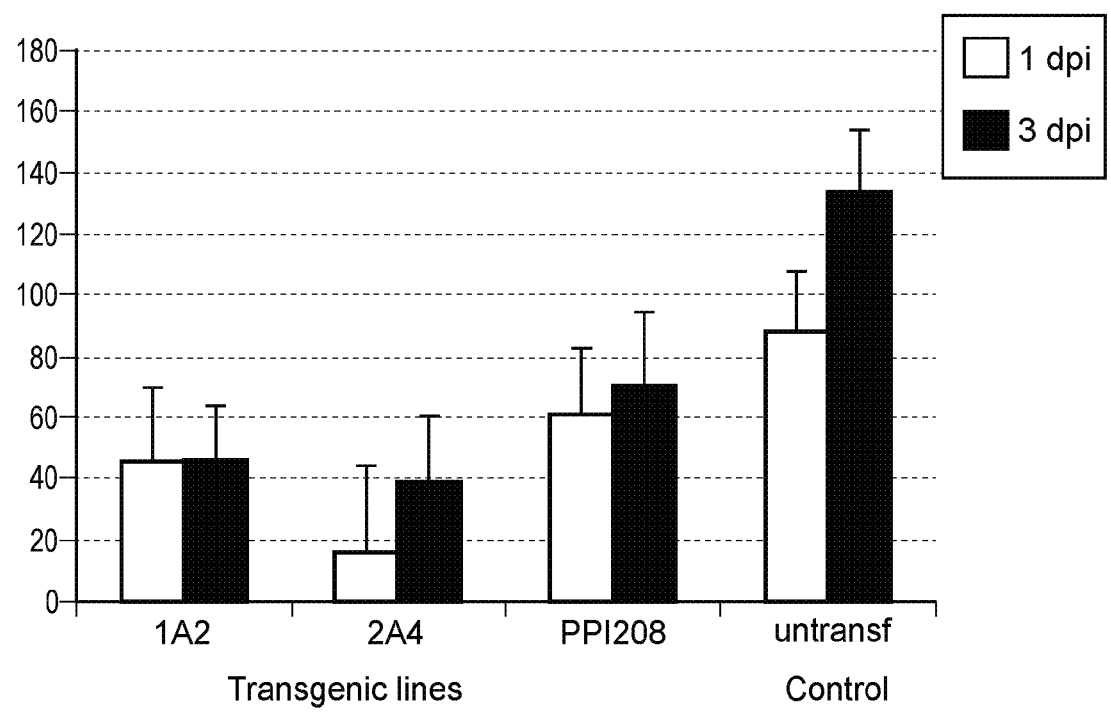

FIG. 14: Effect of transgenic expression of the Hytlo1 gene on tomato resistance to *B. cinerea*. Plants were inoculated with 10 µL of a *B. cinerea* spore suspension 1×106/ml and necrotic area formation was measured after 24 (1 dpi=day post inoculation) and 48 (2 dpi) hours. Values indicate the size of necrotic area (mm2).

Figure 15:
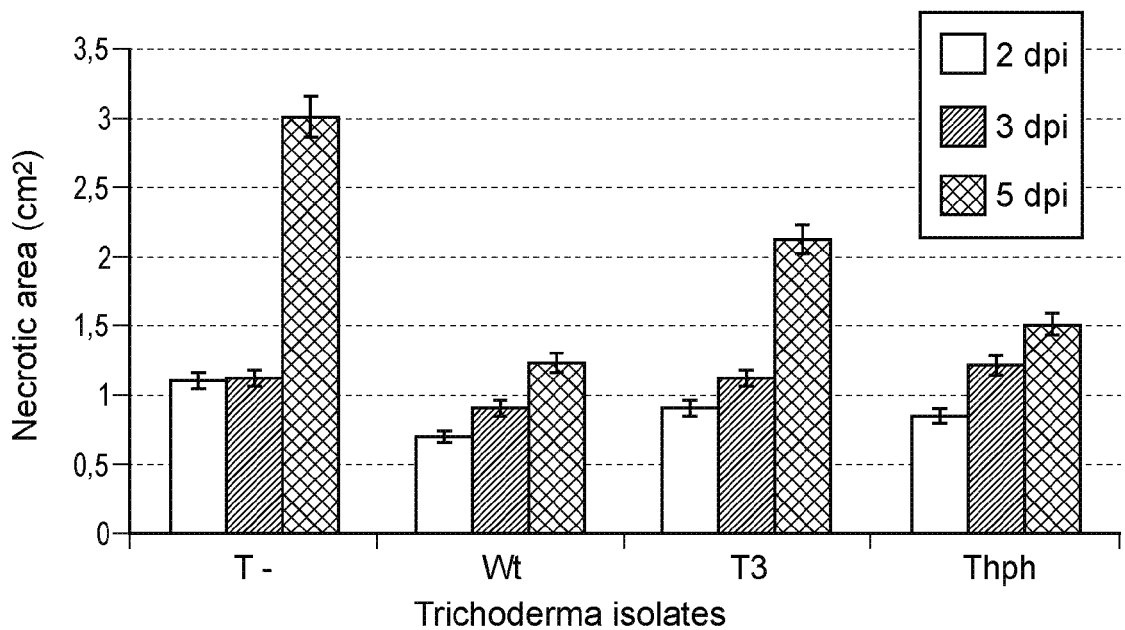

FIG. 15. Effect of Hytlo1 knock-out on the in vivo biocontrol activity of *T. longibrachiatum*. The wild-type strain (Wt), 1 representative ΔHytra1 mutant (T3) and an empty vector-transformed control were applied as a seed coating. Untreated controls (T-) and *Trichoderma*-treated tomato plants were infected with *B. cinerea* by inoculating the third true leaf with 10 µL of a 1×10⁶/ml spore suspension of the pathogen. Inoculated plants were enveloped in transparent plastic bags to achieve high relative humidity conditions and incubated in a growth chamber at 18° C. with a photoperiod of 16 h light. The disease spread was recorded at 2 (2 dpi), 3 (3 dpi) and 5 (5 dpi) days post infection, by measuring necrotic lesions with an electronic caliper and calculating the area as an ellipse. Values are means with SD obtained from at least three different experiments with five replicates and a total of 15 treated plants per treatment.

Figure 16:
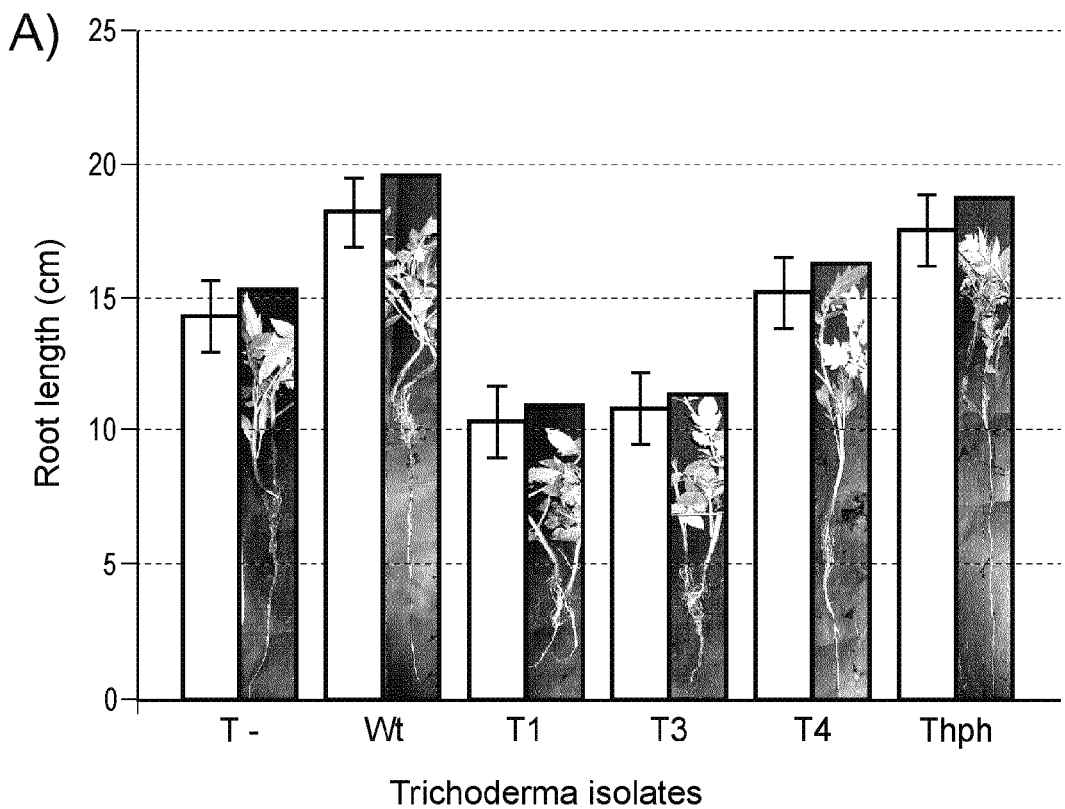
Figure 16:
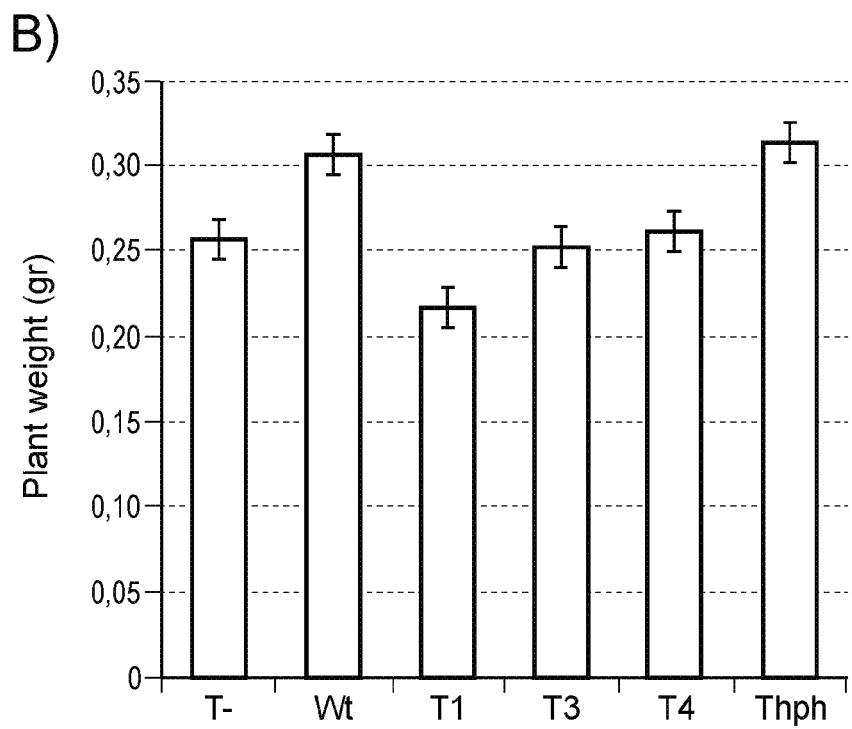

FIG. 16: Effects of Hytlo1 gene knock-out on the plant growth promotion activity of *T. longibrachiatum* strain MK1-KV966 (A, effect on the roots; B, effect on the entire plant). *Trichoderma* seed treatments were: untreated control (T-), wild type *T. longibrachiatum* (wt); Hytlo1 mutants (Ti, T3, T4), empty vector control (Thph). Bars indicate standard deviation from three experiments with four replicates per treatment.

Figure 17:
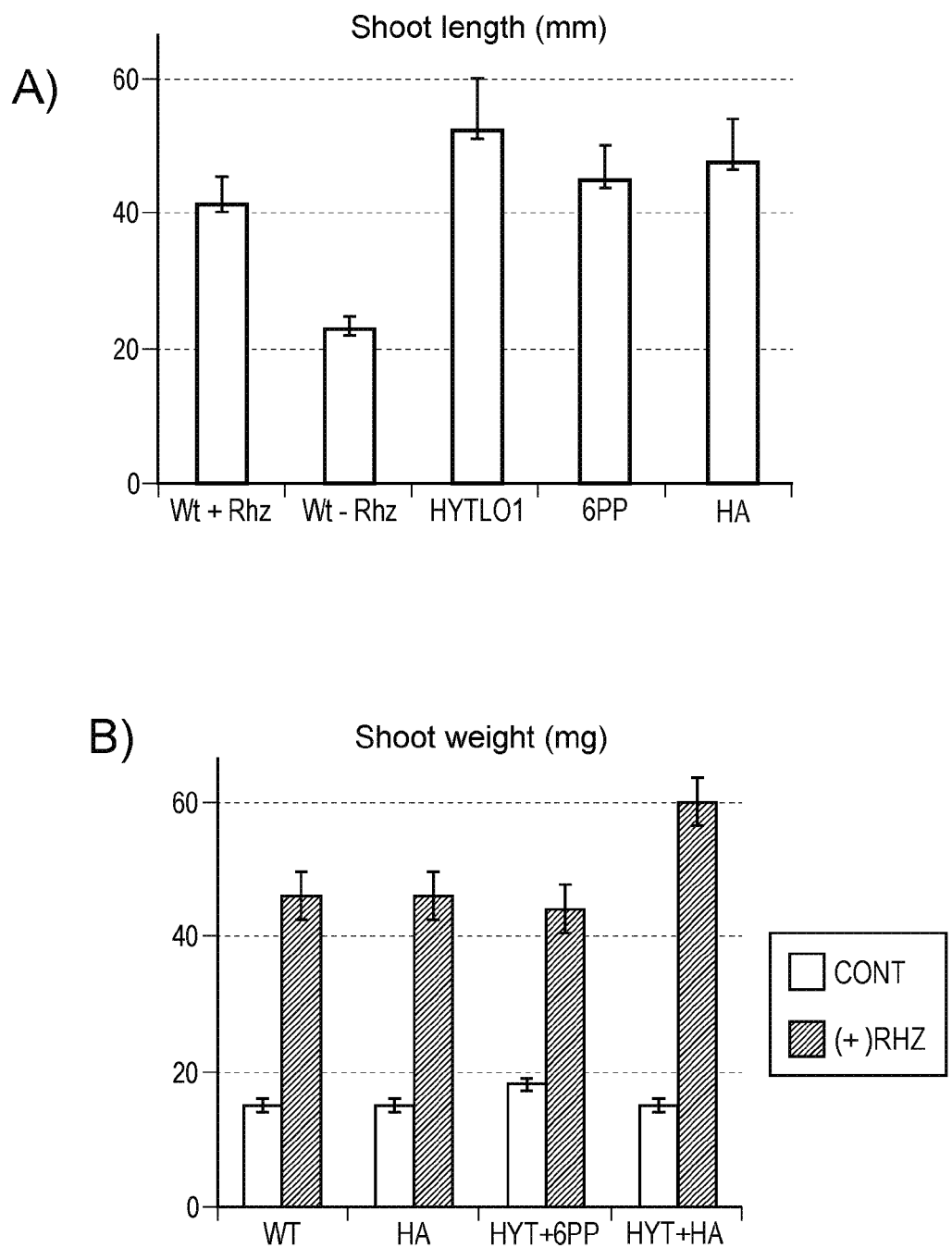
Figure 17:
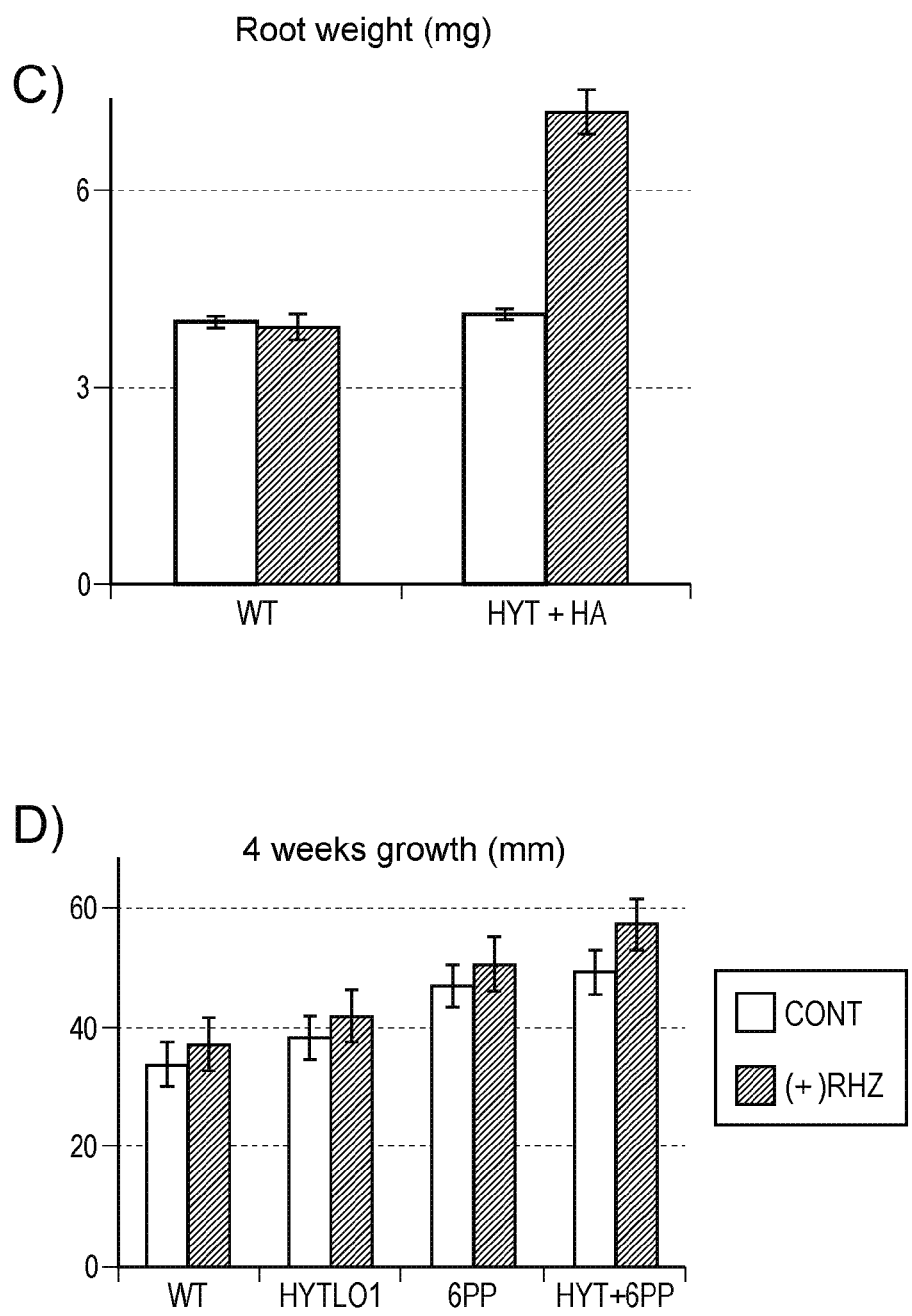

FIG. 17: Enhancement of the effect of *Rhizobium lotii* on *Lotus japonicus* plants by the application of *Trichoderma* metabolites (HYT=HYTLO1 at 0.07 µM, 6PP at 0.002 µM, HA=Harzianic Acid at 0.001 µM). Wt+Rhz=treatment with *R. loti*, Wt-Rhz without *R. loti*. (D) Growth measured after 4 weeks, in the absence (cont) or presence of Rhizoba *R. loti* ((+) Rhiz). The purified molecules were added to the sterile MS media and poured into Petri dishes. Data were recorded 4 weeks after seeding of *L. japonicus*.

Figure 18:
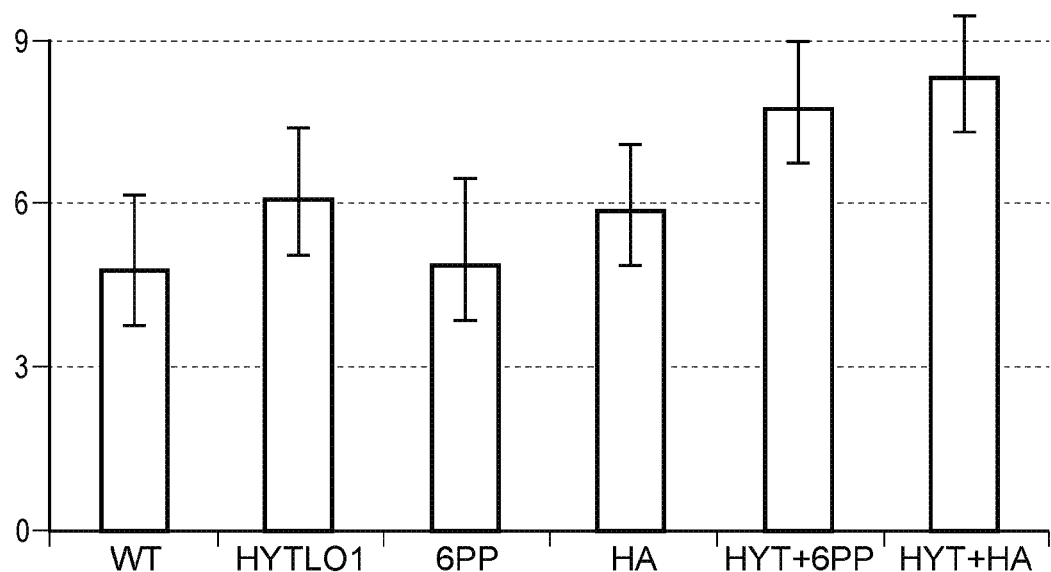

FIG. 18. Enhancement of nodule formation by treatment of *R. lotii* acting on *L. japonicus* by adding different metabolites from *Trichoderma* spp. (HYT=HYTLO1 at 0.07 µM, 6PP at 0.002 µM, HA=Harzianic Acid at 0.001 µM). Wt=control with *R. loti* without metabolites. The purified molecules were added to the sterile MS media and poured into Petri dishes. Average number of nodules per cm of root are indicated. Data were recorded 4 weeks after seeding of *L. japonicus*.

DETAILED DESCRIPTION OF THE INVENTION

*Trichoderma* species are known for their beneficial effects on plant health and plant growth. However, the recorded benefits of *Trichoderma* species is mostly restricted to *T. harzianum, T. virens, T asperellum* and *T. atroviride. T. longibrachiatum* in general is less considered in association with beneficial effects on plants or for use as biocontrol agent. Instead this species is scientifically described and commercially used in relation to the production of plant biomass degrading enzymes. The inventors of the present invention however have surprisingly found that *T. longibrachiatum* is able to produce a bioactive hydrophobin, designated HYTLO1, that has a distinct positive effects on plants. In addition HYTLO1 has negative effects on various plant pathogens. Thus HYTLO1 may be used in the treatment of plants. Positive effects of *T. longibrachiatum* on plants may be selected from plant growth modulation and/or disease control, including disease prevention, and/or stimulation of systemic resistance.

Modulation should be understood as any change or alteration including alterations that can be considered as improvements (increases), but also alterations that may be considered as reductions (decreases). Modulations that can be considered as improvements or increases (stimulations) are preferred. As the skilled person will understand plant growth modulation may be understood as referring to modulation of growth parameters of plants. The modulation of plant growth parameters may be established with reference to an untreated control. For example the plant growth parameter may be root development. Root development may be assessed with any method known to the skilled person, for example as exemplified in the examples. According to particular embodiments the plant growth modulation is improvement (stimulation) of root nodulation in a plant from the family Leguminosae (or alternatively named Fabaceae). The skilled person will know and understand that root nodules are root organs of Leguminosae containing symbiotic *Rhizobia* capable of fixing atmospheric nitrogen. Root nodulation is the process of root nodule formation. The plant from the family Leguminosae may be selected as presented previously. *Glycine max* (soy bean) is selected with particular preference in connection to the stimulation of root nodulation. Stimulation (improvement) of nodulation may be an increase of the nodule density and may be assessed on the basis of this, as is exemplified in the examples.

An alternative plant growth parameter that may be modulated is the germination percentage. The germination percentage may be assessed with any method known to the skilled person, for example by using an hemocytometer Yet a further growth parameter that may be modulated is the germination speed. The germination speed may be assessed with any method known to the skilled person, for example by using an hemocytometer.

It has been found that *T. longibrachiatum* in addition to modulation of plant growth also has beneficial effects on disease control. Disease control should be understood as meaning to include both disease prevention and/or treatment of a disease. Diseases that may be effectively controlled with *T. longibrachiatum* include, but are not restricted to fungal diseases, such as fungal diseases caused by soil-borne fungal pathogens such as *Rhizoctonia* spp., for example *Rhizoctonia solani, Fusarium* spp. *Fusarium graminearum, Pythium* spp. for example *Pythium ultimum*, or fungal diseases caused by aerial-borne fungal pathogens such as *Alternaria* spp. *Alternaria alternata, Botrytis* spp. for example *Botrytis cinerea*, but also diseases caused by bacterial pathogens such as *Xantomonas* spp. for example *Xantomonas campestris*, Disease control may proceed by direct effects on the plant pathogen, but may also proceed via stimulation of systemic resistance. Induced systemic resistance (ISR) of plants is a phenomenon well known to the skilled person wherein, elicited by a local infection, plants respond with a signalling cascade that leads to the systemic expression of a broad spectrum and long lasting disease resistance that is efficient against amongst others fungi, bacteria and viruses. Induced systemic resistance is amongst others associated with the activation of plant defence responses, which may include "oxidative burst", synthesis of phytoalexins, accumulation of PR (Pathogenesis-Related) proteins, localized programmed cell death also known as HR (Hypersensitive Response), etc.

The plant selected for treatment may be any plant, in particular a plant from a commercially relevant crop. The plant may be selected as any plant in a particular commercially relevant plant, such as a plant of a food crop, an ornamental plant, a flower plant. For example the plant may be selected from the family Solanaceae, in particular from the subfamily Solanoideae, such as from the genus *Solanum*, for example *Solanum lycopersicum* (tomato), *Solanum melongena* (egg plant), *Solanum tuberosum* (potato), from the genus *Capsicum*, such as *Capsicum annuum* or *Capsicum frutescens*, from the genus *Physalis* such as *Physalis philadelphica* (tomatillo), but also from the genus *Petunia*, the genus *Browallia*, the genus *Lycyanthes* or the subfamily Nicotianoideae such as from the Genus *Nicotinia*, such as *Nicotinia tabacum*, or the family Brassicaceae, such as *Brassica oleracea, Brassica rapa, Brassica napus, Brassica nigra, Brassica hirta*, from the family Cucurbitaceae, such as from the genus *Cucurbita*, for example *Cucurbita pepo*, the genus *Citrullus*, for example *Citrulles lanatus*, the genus *Cucumis*, for example *Cucumis sativus*, or from the family Leguminosae, such as from the genus *Glycine*, for example *Glycine max* (soy bean), from the genus *Phaseolus*, from the genus *Pisum*, for example *Pisum sativum* (pea), from the genus *Cicer*, for example *Cicer arietinum*, from the genus *Medicago*, for example *Medicago sativa* (alfafa), from the genus *Arachis*, for example *Arachis hypogaea* (peanut), from the genus *Ceratonia*, for example *Ceratonia siliqua* (carob), from the genus *Glycyrrhiza*, for example *Glycyrrhiza glabra* (liquorice), or from the genus *Lupinus*, for example *Lupinus angustifolius*. The skilled person will know that of the plant species mentioned above, various varieties are available for cultivation. Reference to a specific plant species is to be considered as including the various varieties available. The selected plant may be in any developmental stage such as a seed, a seedling, a young developing plant, or a full grown plant.

The inventors of the present invention have found that the above effects of *T. longibrachiatum* on plants are linked to the HYTLO1 protein having the amino acid sequence of SEQ ID NO: 1. This protein has been found in the secreotome of the *T. longibrachiatum* strain MK1. However, it is believed that additional *T. longibrachiatum* strains may express proteins having amino acid sequences similar to the HYTLO1 protein. Thus the invention in general relates to the use of *Trichoderma longibrachiatum* for the treatment of a plant. The *Trichoderma longibrachiatum* is in particular from a strain comprising an autologous nucleotide sequence coding for a protein having at least 70% sequence similarity with the amino acid sequence of SEQ ID NO: 1, such as *Trichoderma longibrachiatum* strain MK1. The nucleotide sequence coding for the amino acid sequence may be the sequence of SEQ ID NO: 2.

As the skilled person will understand from his knowledge of molecular biology, a nucleotide sequence coding for protein sequences may be a DNA sequence and/or a RNA sequence. The skilled person will furthermore understand that an autologous nucleotide sequence is a nucleotide sequence present in the autologous genome of an organism, i.e. it is not introduced from an external source viz. it is not a heterologous sequence. Thus the *T. longibrachiatum* used in the invention is not genetically modified in respect of the HYTLO1 protein. Preferably the selected *T. longibrachiatum* does not comprise any artificially introduced foreign nucleotide sequences i.e. it is a non-GM organism.

The autologous nucleotide sequence codes for a protein having at least 70% sequence similarity with the amino acid sequence of SEQ ID NO: 1. Within the present invention at least 70% similarity should be understood as meaning over 70%, such as at least 75%, at least 80%, at least 85%, at least 90%, at least 95%, at least 97%, at least 99% sequence similarity.

As the skilled person will understand, "sequence similarity" refers to the extent to which individual nucleotide or peptide sequences are alike. The extent of similarity between two sequences is based on the extent of identity combined with the extent of conservative changes. The percentage of "sequence similarity" is the percentage of amino acids or nucleotides which is either identical or conservatively changed viz. "sequence similarity"=(% sequence identity)+(% conservative changes).

For the purpose of this invention "conservative changes" and "identity" are considered to be species of the broader term "similarity". Thus whenever, the term sequence "similarity" is used it embraces sequence "identity" and "conservative changes". According to certain embodiments the conservative changes are disregarded and the % sequence similarity refers to % sequence identity.

The term "sequence identity" is known to the skilled person. In order to determine the degree of sequence identity shared by two amino acid sequences or by two nucleic acid sequences, the sequences are aligned for optimal comparison purposes (e.g., gaps can be introduced in the sequence of a first amino acid or nucleic acid sequence for optimal alignment with a second amino or nucleic acid sequence). Such alignment may be carried out over the full lengths of the sequences being compared. Alternatively, the alignment may be carried out over a shorter comparison length, for example over about 20, about 50, about 100 or more nucleic acids/bases or amino acids.

The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The degree of identity shared between sequences is typically expressed in terms of percentage identity between the two sequences and is a function of the number of identical positions shared by identical residues in the sequences (i.e., % identity=number of identical residues at corresponding positions/total number of positions×100). Preferably, the two sequences being compared are of the same or substantially the same length.

The percentage of "conservative changes" may be determined similar to the percentage of sequence identity. However, in this case changes at a specific location of an amino acid or nucleotide sequence that are likely to preserve the functional properties of the original residue are scored as if no change occurred.

For amino acid sequences the relevant functional properties are the physico-chemical properties of the amino acids. A conservative substitution for an amino acid in a polypeptide of the invention may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without substantially altering the activity of a protein, particularly in regions of the protein that are not directly associated with biological activity (see, e.g., Watson, et al., Molecular Biology of the Gene, The Benjamin/Cummings Pub. Co., p. 224—4th Edition 1987). For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr and vice versa so that a free —OH is maintained; and Gln for Asn and vice versa to maintain a free —NH2.

Exemplary conservative substitutions in the amino acid sequence of SEQ ID NO: 1 can be made in accordance with those set forth below as follows:
Exemplary Conservative Amino Acid Substitutions

| Original residue | Conservative substitution |
| --- | --- |
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

For nucleotide sequences the relevant functional property is mainly the biological information that a certain nucleotide carries within the open reading frame of the sequence in relation to the transcription and/or translation machinery. It is common knowledge that the genetic code has degeneracy (or redundancy) and that multiple codons may carry the same information in respect of the amino acid for which they code. For example in certain species the amino acid leucine is coded by UUA, UUG, CUU, CUC, CUA, CUG codons (or TTA, TTG, CTT, CTC, CTA, CTG for DNA), and the amino acid serine is specified by UCA, UCG, UCC, UCU, AGU, AGC (or TCA, TCG, TCC, TCT, AGT, AGC for DNA). Nucleotide changes that do not alter the translated information are considered conservative changes.

The skilled person will be aware of the fact that several different computer programs, using different mathematical algorithms, are available to determine the identity between two sequences. For instance, use can be made of a computer program employing the Needleman and Wunsch algorithm (Needleman and Wunsch, Journal of Molecular Biollogy, 48, 443-453). According to an embodiment the computer program is the GAP program in the Accelrys GCG software package (Accelrys Inc., San Diego U.S. A). Substitution matrices that may be used are for example a BLOSUM 62 matrix or a PAM250 matrix, with a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

According to an embodiment the percent identity between two nucleotide sequences is determined using the GAP program in the Accelrys GCG software package (Accelrys Inc., San Diego U.S. A) A NWSgapdna CMP matrix and a gap weight of 40, 50, 60, 70, or 80 and a length weight of 1, 2, 3, 4, 5, or 6 is used.

In another embodiment, the percent identity of two amino acid or nucleotide sequences is determined using the algorithm of E. Meyers and W. Miller (Meyers and Miller, 1989, Bull. Math. Biol. 51, 5-37) which has been incorporated into the ALIGN program (version 2.0) (available at the ALIGN Query using sequence data of the Genestream server IGH Montpellier France http://vegajgh.mrs.fr/bin align-guess.cgi) using a PAM120 weight residue table, a gap length penalty of 12 and a gap penalty of 4.

For the present invention it is most preferred to use BLAST (Basic Local Alignment Tool) to determine the percentage identity and/or similarity between nucleotide or amino acid sequences.

Queries using the BLASTn, BLASTp, BLASTx, tBLASTn and tBLASTx programs of Altschul et al. (1990) may be posted via the online versions of BLAST accessible via http://www.ncbi.nlm.nih.gov. Alternatively a standalone version of BLAST {e.g., version 2.2.24 (released 23 Aug. 2010)) downloadable also via the NCBI internet site may be used. Preferably BLAST queries are performed with the following parameters. To determine the percentage identity and/or similarity between amino acid sequences: algorithm: blastp; word size: 3; scoring matrix: BLOSUM62; gap costs: Existence: 11, Extension: 1; compositional adjustments: conditional compositional score matrix adjustment; filter: off; mask: off. To determine the percentage identity and/or similarity between nucleotide sequences: algorithm: blastn: word size: 11; max matches in query range: 0; match/mismatch scores: 2, −3; gap costs: Existence: 5, Extension: 2; filter: low complexity regions; mask: mask for lookup table only.

The percentage of "conservative changes" may be determined similar to the percentage of sequence identity with the aid of the indicated algorithms and computer programs. Some computer programs, e.g., BLASTp, present the number/percentage of positives (=similarity) and the number/percentage of identity. The percentage of conservative changes may be derived therefrom by subtracting the percentage of identity from the percentage of positives/similarity (percentage conservative changes=percentage similarity−percentage identity).

It should be noted that an amino acid sequence having over 70% sequence similarity with the amino acid sequence of SEQ ID NO: 1 is disclosed in the art with Genbank accession number EF419429. This protein (and the nucleotide sequence coding for it) is identified as originating from *Trichoderma harzianum* T22. However, further analysis based on molecular tests performed by the inventors of the present invention has shown that *Trichoderma harzianum* T22 does not comprise any nucleotide sequence coding for an amino acid sequence having over 70% sequence similarity with the amino acid sequence of SEQ ID NO: 1. Thus the disclosure of Genbank entry EF419429 is incorrect and not enabled in respect of the source of the nucleotide and amino acid sequences presented.

According to certain embodiments the use of *Trichoderma longibrachiatum* is combined with the use of one or more plant biostimulants selected from (i) a *Trichoderma* species other than *Trichoderma longibrachiatum*, (ii) harzianic acid or a biologically active isomer thereof, such as, iso-harzianic acid, (iii) 6-pentyl-α-pyrone or (iv) *Rhizobia*. HA, iso-HA and 6PP are known metabolites of *Trichoderma* species having beneficial effects on plants. Combined with *Trichoderma longibrachiatum* and in particular the HYTLO1 protein from *Trichoderma longibrachiatum* or a similar protein further different *Trichoderma* species, such phytostimulatory agents provide additional effects on plants in respect of (a) plant growth modulation, such as improvement of plant fresh weight, improvement of plant dry weight, improvement of root development, including improved nodulation in Leguminosae, increase of germination percentage and/or increase of germination speed, or (b) disease control such as via anti-microbial activity, preferably antifungal activity, or via stimulation of systemic resistance. These additional effects according to certain embodiments may extend to synergistic levels.

*Trichoderma* species different from *Trichoderma longibrachiatum* having plant stimulatory features may be readily identified by the skilled person and may for example be selected from *T. harzianum* (for example strain T22), *T. atroviride* (for example strain P1), *T. asperellum*, *T. virens* (for example strain GV41).

Harzianic acid (CAS: 157148-06-6) or alternatively HA is an alkaloid compound of the structural formula (1) below, having the chemical formula $C_{19}H_{27}NO_6$ and a MW of 365.42.

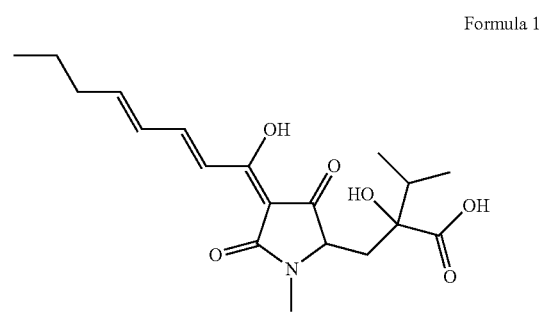 [SMILES: CCC/C=C/C=C/C(O)=C1/C(=O)C(CC(O)(C(=O)O)C(C)C)N(C)C1=O]

Formula 1

HA is commercially marketed by various parties and may amongst others be obtained in a suitable form from CHEMFACES (http://www.chemfaces.com/natural/Harzianic-acid-CFN00118.html). Within the context of the present invention the term harzianic acid includes all stereochemical isomers of the compound of formula 1, such as iso-harzianic acid.

Iso-Harzianic acid or alternatively iso-HA is a stereoisomer of HA with the structural formula (2) below, having the chemical formula $C_{19}H_{27}NO_6$ and a MW of 365.42.

Formula 2

$C_{19}H_{27}NO_6$
Exact Mass: 365,18384
Mol. Wt: 365,42078
2-Hydroxy-2-[4-(1-hydroxy-octa-2,4-dienylidene)-
1-methyl-3,5-dioxo-pyrrolidin-2-ylmethyl]-
3-methyl-butyric acid 6-Pentyl-α-pyrone (CAS: 27593-23-3) or alternatively 6PP is a compound of the structural formula (3) below having the chemical formula $C_{10}H_{14}O_2$ and a MW of 166.216. It is commercially marketed by various parties and may amongst others be obtained in a suitable form from SIGMA.

Formula 3

*Rhizobia* are nitrogen-fixing bacteria capable of living in a symbiotic relationship with plants from the family Leguminosae. The skilled person will know that *Rhizobia* may have a certain host specificity and it is within the ambit of the knowledge of the skilled person to select *Rhizobia* capable of living in a symbiotic relationship with a selected plant from the family Leguminosae. According to the present invention any *Rhizobia* may be used that have specificity for a selected plant from the family Leguminosae, such as from the genus *Glycine*, for example *Glycine max* (soy bean), from the genus *Phaseolus*, from the genus *Pisum*, for example *Pisum sativum* (pea), from the genus *Cicer*, for example *Cicer arietinum*, from the genus *Medicago*, for example *Medicago sativa* (alfalfa), from the genus *Arachis*, for example *Arachis hypogaea* (peanut), from the genus *Ceratonia*, for example *Ceratonia siliqua* (carob), from the genus *Glycyrrhiza*, for example *Glycyrrhiza glabra* (liquorice), or from the genus *Lupinus*, for example *Lupinus angustifolius*. The *Rhizobia* for example may be selected from the genus *Rhizobium* such as *R. leguminosarum, R. tropici, R. loti, R. trifolii, R. meliloti, R. fredii, R. cellulosilyticum, R. daejeonense, R. etli, R. galegae, R. gallicum, R. giardinii, R. hainanense, R. huautlense, R. indigoferae, R. loessense* o *huanglingense, R. lusitanum, R. mongolense, R. sullae* o *hedysari, R. undicola* (ex Allorhizobium *undicola*), R. Yanglingense or from the genus *Bradyrhizobium*, such as *B. japonicum, B. elkanii, B. diazoefficiens, B. liaoningense B. yuanmingense, B. canariense* or from the genus *Mesorhizobium* such as *M. albiziae, M. amorphae, M. chacoense, M. ciceri* (ex *Rhizobium ciceri*), *M. huakuii* (ex *Rhizobium huakuii*), *M. loti* (ex. *Rhizobium loti*), *M. mediterraneum* (ex. *Rhizobium mediterraneum*), *M. plurifarium, M. septentrionale, M. temperatum, M. tianshanense* (ex *Rhizobium tianshanense*), or from the genus *Azorhizobium* such as *A. caulinodans, A. doebereinerae* o *johannae* or from the genus *Methylobacterium* such as *M. nodulans* or from the genus *Ensifer* (ex *Sinorhizobium*) such as *E. abri, E. americanum, E. arboris, E. fredii* (ex *Rhizobium fredii*), *E. indiaense, E. kostiense, E. kummerowiae, E. medicae, E. meliloti* (ex *Rhizobium meliloti*), *E. mexicanum, E. morelense* (aka "*E. adhaerens*"), *E. adhaerens, E. saheli* or *sahelense, E. terangae, E. xinjiangense*, or combinations thereof. In view of the commercial importance of this crop, according to certain embodiments selected *Rhizobia* preferably are "soybean *Rhizobia*" capable of forming root nodules in soybean (*Glycine max*), such as for example *Bradyrhizobium japonicum, Bradyrhizobium elkanii, Bradyrhizobium diazoefficiens, Bradyrhizobium liaoningense, Ensifer fredii, Ensifer xinjiangenese, Mesorhizobium tianshanense* or others known to the skilled person.

A further aspect of the invention relates to a composition comprising a carrier and a source of protein having at least 70% sequence similarity with an amino acid sequence according to SEQ ID NO: 1. The composition is characterized in that the protein is an autologous protein from *Trichoderma longibrachiatum*.

The composition preferably is an agronomical composition, for example an agronomical composition aimed at one or more selected from plant growth modulation, such as improvement of plant fresh weight, improvement of plant dry weight, improvement of root development, including improvement of root nodulation in Leguminosae, increase of germination percentage and/or increase of germination speed, or disease control or stimulation of systemic resistance. The carrier may be selected from any suitable carrier, such as an agronomically acceptable carrier. Selection of suitable carriers is within the ambit of the knowledge of the skilled person. Suitable carriers or co-formulants could be clay, sands, active carbon, for solid formulations or lactose/celluloses for immobilization and dispersal of solid and liquid formulations. HYTLO1 and HA could be dissolved in ethanol or methanol at low concentration $10^{-3}$M and diluted in water at $10^{-5}$ to $10^{-6}$ M for the application. 6PP could be dissolved in ethyl acetate or acetone at $10^{-3}$ M to be further dissolved in water to $10^{-5}$ to $10^{-6}$ M for the application. Anti-oxidants such as benzotriazole, benzophenone, acrylate could be added to the composition to increase the shelf-life. Liquid formulations could be added to a solid, spore-based formulation of living *Trichoderma* or other microbe to potentiate the effect. The active principle could be prepared by freeze drying, spray drying, fluid-bed drying, vacuum drying, tray drying or liquid stabilisation by buffering the pH. Finally, the designing of the final formulation could be done, but not limited to, by processing the pure or crude protein in blended mixed in powders or dissolved in liquids or solvents. For application in agriculture, formulations will be optimized so that an amount of 30 ml (30 gr if dried) to 5 Liter (5 kg if dried) of formulated product will be applied for 1 hectare of crop. Application to the crop may be by any known means such as by using drip irrigation systems, drenching, fogging or spraying or any other crop application system.

A source of the protein should be understood as a source suitable to provide the protein. In the composition the source of the protein may be biomass of a *Trichoderma longibrachiatum* strain, such as *Trichoderma longibrachiatum* strain MK1 deposited as CBS 137023, preferably viable biomass. The skilled person will understand that in case the source is selected as viable biomass the protein need not be present but instead may be expressed in situ at a later stage. This is in particular the case when viable spores are selected as the biomass. Alternatively the source of the protein may be a product derived from such biomass, such as an at least partially purified extract. In the composition of the invention the protein preferably is provided from a source wherein it is in a purified state or form. A purified state or form should be understood as a state wherein the protein is more pure than in its original state, i.e. it is cleaned and/or separated from foreign elements and/or elements present in the environment from which it originates. In a purified form or state the protein need not be 100% pure. Instead it may have a purity of for example 40-99.9%, such as 50-99%, or 60-95%, or 70-90%, or 80-90%, or 85-90%.

The content of the protein in the composition may be between 100% w/w (pure protein) and 0.1 ppb ($1\cdot10^{-10}$) or, such as between 10% w/w and 0.1 ppb, between 5% w/w and 1 ppb, between 1% w/w and 5 ppb, between 0.1% w/w and 10 ppb, based on the activity demonstrated in our assays.

Similar to the use of the *Trichoderma longibrachiatum* discussed above, also in the composition, the protein may be combined with one or more plant biostimulants such as selected from (i) a *Trichoderma* species, preferably a *Trichoderma* species other than *Trichoderma longibrachiatum*, (ii) harzianic acid, or a biologically active isomer thereof, such as iso-harzianic acid or (iii) 6-pentyl-α-pyrone. Details about the *Trichoderma* species, HA, iso-HA and 6PP added in addition to the HYTLO1 protein (or a similar protein) are provided above. In the composition of the invention *Trichoderma* species may be added in an amount of from 0.01% to 100% of active ingredient and HA and 6PP added in the same range of concentration as HYTLO1.

A further aspect of the invention relates to the use of a protein having at least 70% sequence similarity with an amino acid sequence according to SEQ ID NO: 1, for the treatment of a plant. This aspect of the invention is characterized in that the protein is provided as an autologous protein from *Trichoderma longibrachiatum*. According to a preferred embodiment of this aspect of the invention wherein the use of the protein is combined with the use of one or more plant biostimulants such as selected from (i) a *Trichoderma* species, preferably a *Trichoderma* species other than *Trichoderma longibrachiatum*, (ii) harzianic acid, or a biologically active isomer thereof, such as iso-harzianic acid or (iii) 6-pentyl-α-pyrone. According to another preferred embodiment the treatment of the plant is aimed at one or more selected from (a) plant growth modulation, such as improvement of plant fresh weight, improvement of plant dry weight, improvement of root development, including improvement of root nodulation in Leguminosae, increase of germination percentage and/or increase of germination speed, or (b) disease control, such as via anti-microbial activity, preferably antifungal activity, or via stimulation of systemic resistance. The technical features of the use of a protein having at least 70% sequence similarity with an amino acid sequence according to SEQ ID NO: 1, for the treatment of a plant and of its various preferred embodiments are similar to those of the other aspects of the invention and have already been discussed above.

A further aspect of the invention relates to a method for producing a protein having at least 70% sequence similarity with an amino acid sequence according to SEQ ID NO: 1. The method comprises:

providing *Trichoderma longibrachiatum* comprising a functional autologous gene coding for the protein;
culturing biomass of *Trichoderma longibrachiatum* under conditions suitable for expression of the gene
obtaining the protein from the biomass culture.

In the method *Trichoderma longibrachiatum* comprising a functional autologous gene coding for the protein having at least 70% sequence similarity with an amino acid sequence according to SEQ ID NO: 1 is provided. On the basis of the provided sequences the skilled person is able to determine whether or not a certain *T. longibrachiatum* strain comprises a functional autologous gene coding for the protein. According to certain embodiments of the method according to the invention and the other aspects of the invention, it is preferred to use a *T. longibrachiatum* strain devoid of artificially inserted foreign (heterologous) DNA i.e. a non-GM strain. For example *T. longibrachiatum* strain MK1 may be selected. As the skilled person will understand, in the non-GM *T. longibrachiatum* strain and any protein isolated therefrom any nucleotide sequences present will be free of nucleotide sequences from a different organism. As is known, products obtained by the use of genetic modification (GM or GMO products) are received with reservations and even banned by certain consumer groups. In addition in various jurisdictions special regulations may apply to bringing GM organisms and products derived therefrom in the environment. In view of this, non-GM production has certain benefits. *T. longibrachiatum* may be provided in any suitable viable form, such as in the form of spores and/or hyphal biomass.

In the method of the invention biomass of *T. longibrachiatum* is cultured under conditions suitable for expression of the gene. Culturing may be in a solid state fermentation or a liquid fermentation or semi-solid fermentation. According to certain embodiments it is preferred to culture *T. longibrachiatum* in a liquid fermentation. The skilled person will be able to determine suitable culture conditions for both solid state fermentations and liquid fermentation to allow growth of *T. longibrachiatum* and expression of the gene. For example *T. longibrachiatum* may be grown on Murashige and Skoog medium+0.8-1.3%, such as 1% sucrose for 6-8, such as 7 days at 23-27° C., such as 25° C. under aeration e.g. by shaking at 150 rpm.

From the biomass culture the protein is obtained. The protein may be obtained in the from of biomass, preferably viable biomass. Alternatively the protein may be isolated from the biomass and/or the culture broth. It is believed that the protein is secreted and is also bound to the fungus structure lining the external surface. Methods for isolation/purification of proteins from cultured biomass are known and/or can be easily developed by the skilled person without an undue burden. For the HYTLO1 protein (and similar proteins) for example the methods presented in example 3 may be used. Other methods based on chromatography techniques that exploit the size or the hydrophobic properties of the proteins may be used. For instance a method to obtain the protein could be either by membrane purification, starting from centrifugating the biomass followed by fractionation of the supernatant fractionation by a membrane filter with a final cutting of 5 kD, thus obtaining the about 7 kD protein. Another method could be based on adsorption chromatography or expanded bed chromatography (Birger et al., 1999, Journal of Chromatography A, 865:129-144). These methods could be integrated by extraction with an appropriated solvent for hydrophobic compounds.

A further aspect of the invention relates to the protein obtainable from the method for producing a protein having at least 70% sequence similarity with an amino acid sequence according to SEQ ID NO: 1. This protein is produced as an autologous protein and may thus may be considered to be a non-GM product, in particular when produced in a *T. longibrachiatum* strain devoid of foreign (heterologous) DNA i.e. a non-GM strain.

According to yet a further aspect, the invention relates to *Trichoderma longibrachiatum* strain MK1 (KV966). This strain comprises an autologous nucleotide sequence coding for a protein having at least 70% sequence similarity with the amino acid sequence of SEQ ID NO: 1 and thus may be used as a source for obtaining this protein, in particular as a non-GM product. It has been deposited with The Centraalbureau voor Schimmelcultures, Utrecht, The Netherlands (CBS) on Dec. 10, 2013 under deposit number CBS 137023. The strain was isolated from natural soil in an agricultural field and it was identified as *Trichoderma longibrachiatum* on the basis of morphological and physiological characteristics. This identity was confirmed on the basis of molecular methods using the internal transcribed spacer (ITS) method (Schoch et al., 2012, PNAS, 109:6241-6246). *Trichoderma longibrachiatum* strain MK1 may be cultured with methods suitable for culturing other *Trichoderma longibrachiatum* strains known to the skilled person, e.g. by using the culture conditions as detailed above and as exemplified in experiment 3. Within this description reference to *Trichoderma longibrachiatum* strain MK1 refers to the strain deposited under deposit number CBS 137023 or any equivalent strain, including derived strains, having its characterising features.

Seeds treated with a source of a protein having at least 70% sequence similarity with an amino acid sequence according to SEQ ID NO: 1, said protein being obtained as an autologous protein from *Trichoderma longibrachiatum* are yet a further aspect of the invention. On the surface of such seeds the protein and/or the protein source will be present. The seed may be from any plant, preferably from a commercially relevant plant as identified above.

A further aspect of the invention relates to a method for producing crop plants which employs the use of a source of the HYTLO1 protein. The method comprises the steps of:
providing the number of crop plants;

treating the number of crop plants with a source of a protein having at least 70% sequence similarity with an amino acid sequence according to SEQ ID NO: 1, said protein provided as an autologous protein from a *Trichoderma longibrachiatum;* providing to the number of crop plants suitable nutrients and environmental conditions to develop.

Figure 1:
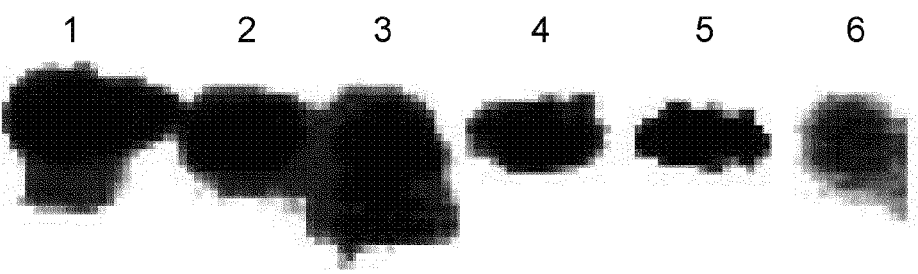
FIG. 1: Expression of *Trichoderma longibrachiatum* Hytlo1 gene on salt medium (SMS)+1% (wt/vol) sucrose (lane 1), SMS+1% (wt/vol) cellulose (lane 2), SMS+1% (wt/vol) chitin (lane 3), SMS+1% (wt/vol) crude extract of tomato leaves (lane 4), SMS+1% (vol/vol) *Rhizoctonia solani* culture filtrate (lane 5), SMS+1% (wt/vol) *R. solani* purified cell walls (lane 6).
Figure 2:
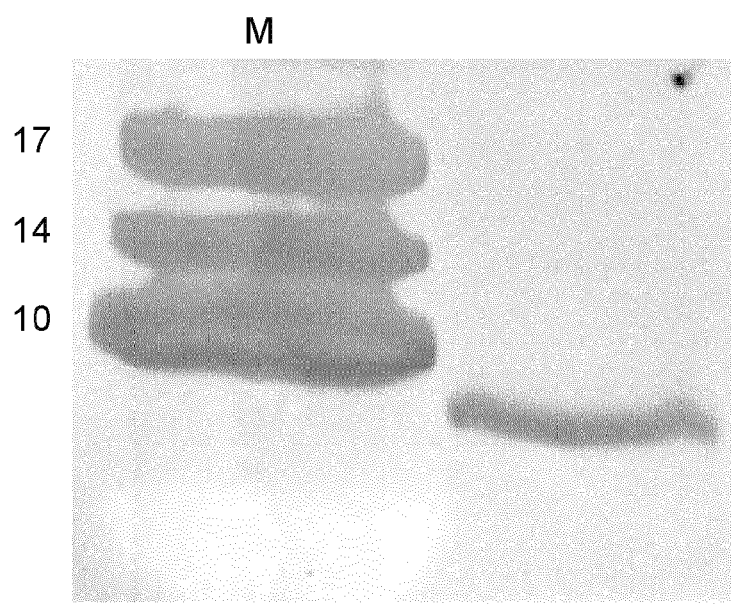
FIG. 2: SDS-PAGE silver stained of purified HYTLO1 (right lane) and molecular markers (left lane) in kD.
Figure 3:
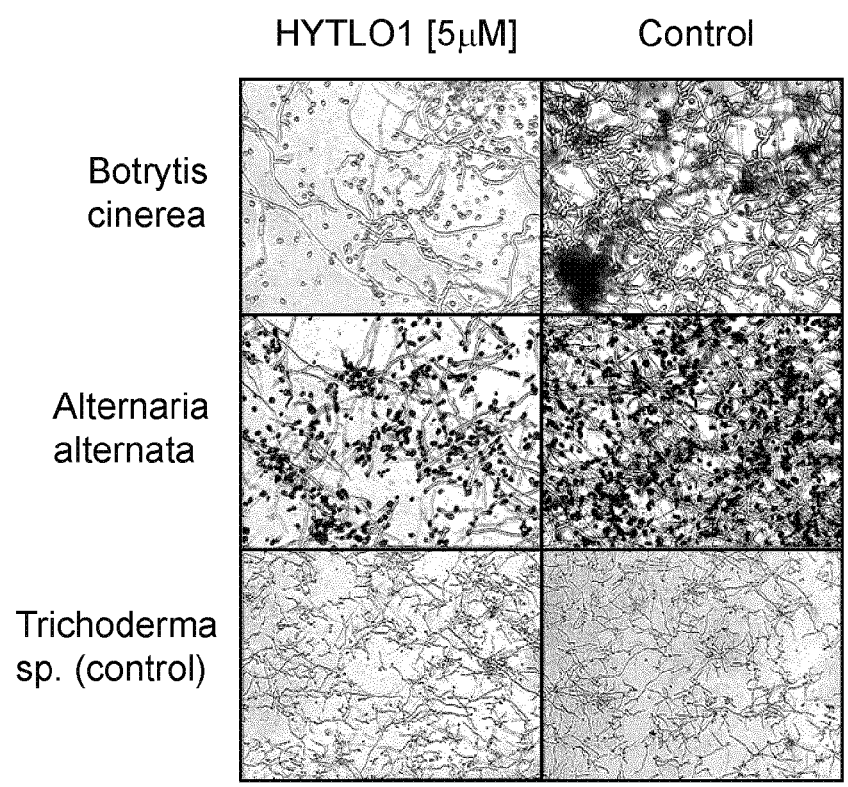
FIG. 3: HYTLO1 antifungal activity. Spore of the pathogens *Botrytis cinerea* and *Alternaria* spp. and of the biocontrol agent *Trichoderma harzianum* strain MK1-KV966 were germinated at 25° C. for 24 hours in Potato Dextrose Broth (PDB) containing 5 μM of HYTLO1 and compared with those germinated in PDB plus the same solvent as the control.
Figure 4:
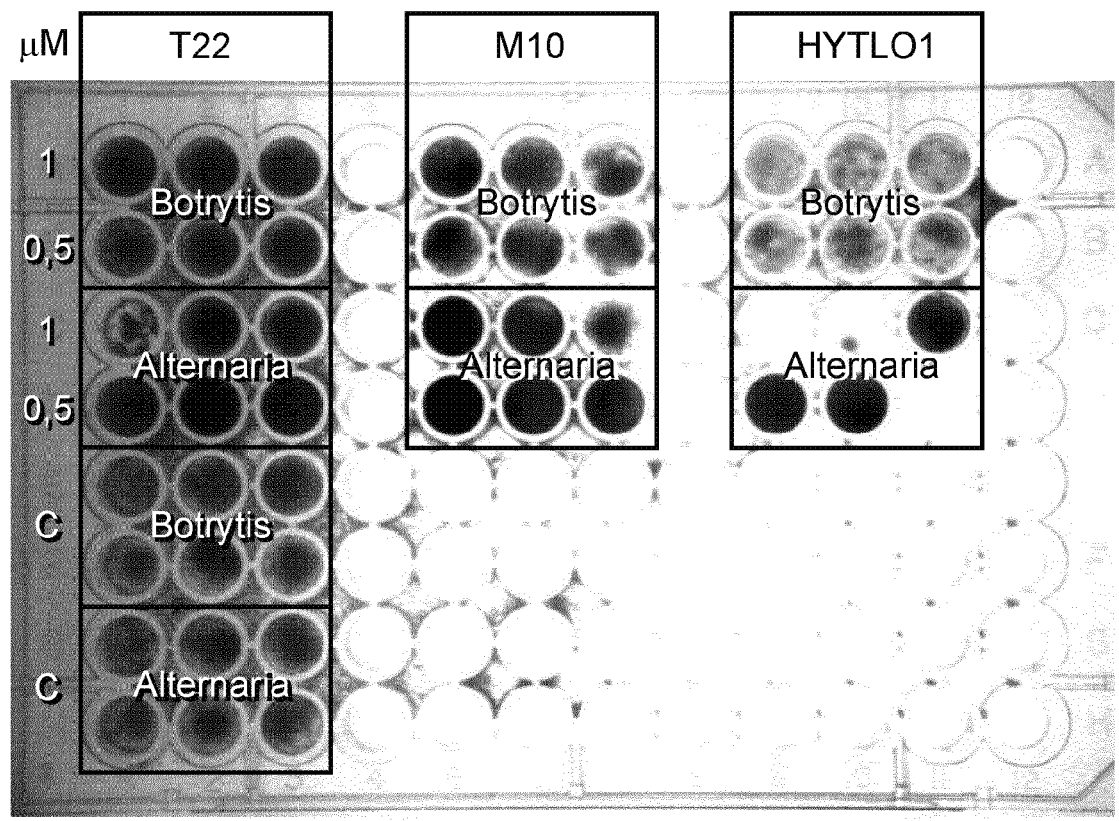
FIG. 4. Antifungal effect of HYTLO1 on *B. cinerea* growth compared to similar hydrophobins purified from *T. harzianum* strain T22 and *T. harzianum* strain M10. Assay protocol is described in Lorito M. et al. 1994. Microbiology UK, 140:623-629. Numbers on the left side indicate micro molar concentration of HYTLO1 used. T22 and M10=hydrophobin from strain T22 and M10, respectively. The inhibition of the pathogen colony is indicated by the reduced intensity of the dark color in the wells compared to control (C).
Figure 5:
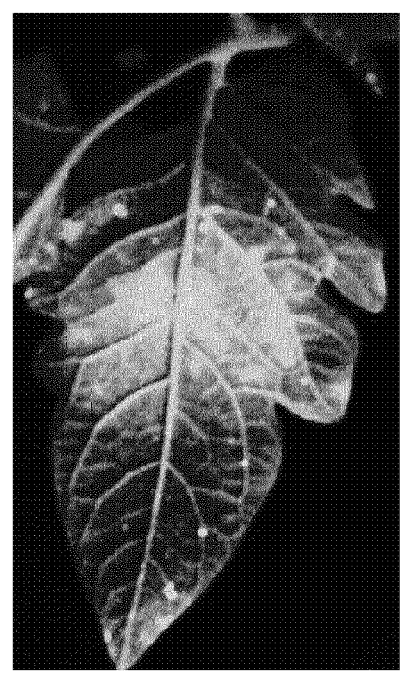
FIG. 5: Effect of purified HYTLO1 (5 μM) injected on tomato leaves after 48 hours under UV light. Fluorescence is due to accumulation of compounds related to plant defense response.
Figure 6:
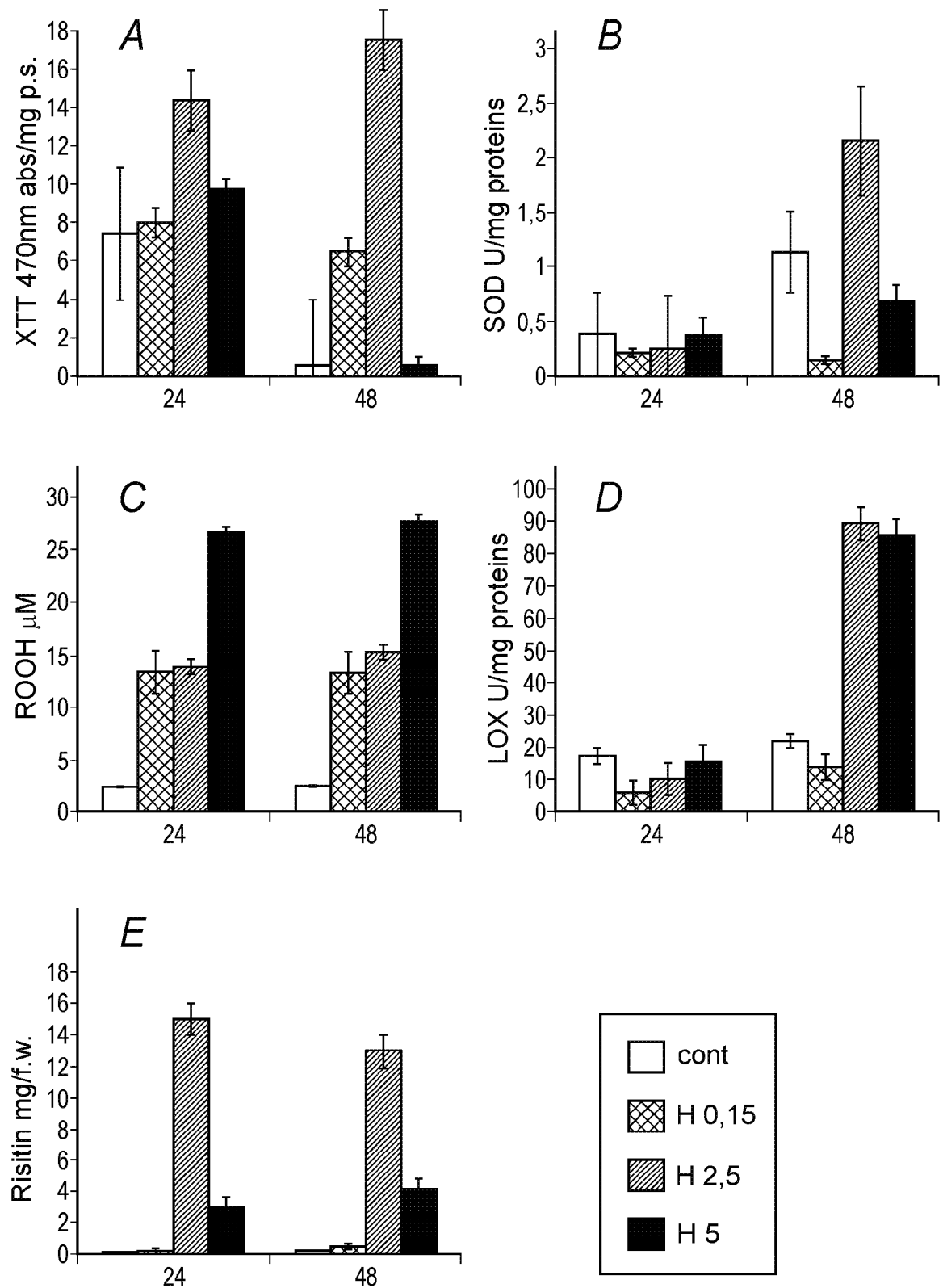
FIG. 6: Effect of purified HYTLO1 (0.15, 2.5, 5.0 mM) on the activation of tomato plant defense responses. Leaves were injected with 10 ml of the protein solution and analyzed after 24 and 48 hours for the production of: (A) anion superoxide (XTT assay, mg p.s.=milligram of dry weight), (B) SOD activity (U/mg proteins), (C) ROOH peroxide accumulation (FOX1 assay), (D) LOX activity, (E) phytoalexin rishitin accumulation (g f.w.=gram of leaf fresh weight). Values are means+S.E. Methods used are the followings. Lyophilized plant tissues (10 mg) from HYTLO1-injected and -non injected tomato leaves were collected at different time points after inoculation (from 6 to 48 h) and homogenized. Anion superoxide was detected by measuring the reduction of 2,3-bis(2-methoxy-4-nitro-5-sulfophenyl)-5-[(phenylamino) carbonyl]-2H-tetrazolium hydroxide (XTT) to formazan, according to Sutherland, M. W., and B. A. Learmonth, 1997, Free Radical Research, 27:283-289, with modifications reported by Castoria, R., et al., 2003, Phytopathology, 93:564-572. Absorbance at 490 nm was measured in a microplate reader. XTT levels were expressed as mean absorbance values mg-1±standard errors. The activities of SOD, pH 7.8 and 10.0 (EC 1.15.1.1) and LOX enzymes (EC 1.13.11.12) were quantified as described by Reverberi M, et al., 2005, Free Radical Research, 39:637-647. Total hydroperoxides (ROOH) were detected by using the FOX spectrophotometric assay by monitoring the oxidation of xylenol orange at 560 nm (Ferrous ion oxidation xylenol orange: FOX-1) (Banerjee D, et al., 2003, Clinica Chimica Acta, 337:147-152). Quantification of the phytoalexins rishitin was performed by treating the leaf samples with methylene chloride (2 ml) in the presence of 100 mg of BHT. The tubes were left in a fume hood for 15/20 minutes and occasionally shaken. The extracts were filtered on filter paper Whatmann 3 MM and dried under nitrogen flow. Rishitin was quantified by GC-MS as described in Fanelli et al., 1992, Natural Toxins 1: 136-146.
Figure 7:
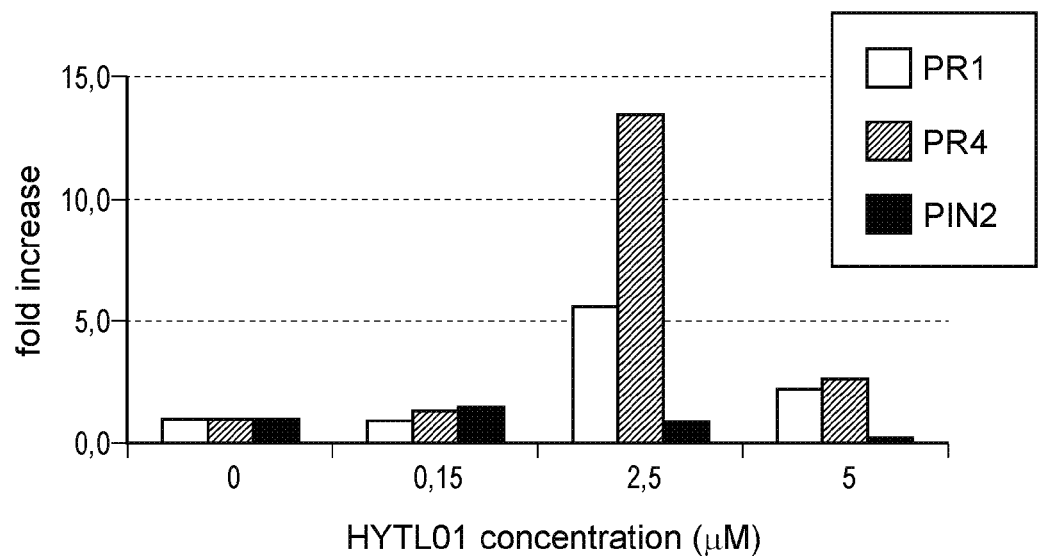

In the method a number of plants is provided. A number of should be understood as meaning one or more and includes in particular a plurality. The plants may be selected as any plant in particular commercially relevant plants as identified above. Again, the skilled person will know that of the plant species mentioned above, various varieties are available for cultivation. Reference to a specific plant species is to be considered as including the various varieties available. The plants may be provided as seeds, seedlings or young developing plants.

In the method the provided number of plants is treated with a source of the HYTLO1 protein. Treatment may comprise contacting the plant with the protein source. For example seeds, seedlings of developing plants may be contacted with the protein source by applying a liquid solution comprising the protein source. The liquid solution may be applied by means of soaking as a drench, by watering or by spraying. The liquid solution may have a content of the protein ranging from pure protein to $1\times10^{-11}$ M, such as 50% w/v to $1\times10^{-9}$ M, preferably $1\times10^{-3}$ M to $1\times10^{-9}$ M, such as $1\times10^{-5}$ M to $1\times10^{-8}$ M, more preferably $5\times10^{-6}$ M to $1\times10^{-7}$ M.

In the method the number of plants is provided with suitable nutrients and environmental conditions to allow the plant to develop further. The selection of suitable nutrients (such as N, P, S, $CO_2$) and environmental conditions (such as a suitable root substrate, suitable temperature and suitable light conditions) is within the ambit of the knowledge of the skilled person.

The invention will now be further illustrated and clarified with reference to the following exemplary experiments.

EXPERIMENTS

1. Isolation and Sequence Analysis of HYTLO1 Protein and the Hytlo1 Gene from *Trichoderma longibrachiatum* Strain MK1

*T. longibrachiatum* low molecular weight secretome was analysed by SDS-PAGE. A protein with an estimated molecular weight of about 8 kDa resulted to be profusely secreted when *T. longibrachiatwn* was grown in liquid media added with plant tissue, fungal biomass or cellulose. The band, corresponding to this protein, was excised from the SDS-PAGE gel and sequenced by Edman reaction process. The first 15 amino acidic residues of the protein were obtained. Blastp analysis of this peptide provides intermediate level homologies with hydrophobin from various fungi including *T. reesei, T. harzianum, Cladosporium fulvum, Ophiostoma ulmi, Claviceps pwpurea* and *Magnaporthe grisea*. Degenerated primers were synthesized according to the identified amino acidic residues and a 3' race was performed. The PCR products were cloned in pGEMt-Easy vector and sequenced. The blastx analysis of one of the obtained sequence, 445 bp long named Hytlo 1 (SEQ ID NO:2), showed homology with class II fungal hydrophobins. Hytlo1 cDNA sequence resulted 216 bp long and the in silico translation gave a predicted protein of 71 aa (SEQ ID NO: 1), with a molecular weight of 7218 Da and 8 cysteine residues arranged in the strictly conserved hydrophobin motif $X_n$-C-$X_{5-10}$-C-C-$X_{11-44}$-C-$X_{8-23}$-C-$X_{5-9}$-C-C-$X_{6-18}$-C-$X_m$ (SEQ ID NO:5). The genomic copy of the Hytlo1 gene was obtained by PCR amplification performed on *T. longibrachiatum* genomic DNA, by using the primers Hytlo1For (GCTGTCTGCCCTACCGGCC; SEQ ID NO:3) and Hytlo1Rev (TTACTGGGTGCCGAGGGC; SEQ ID NO:4) designed at the 5' and 3' of Hytlo1 cDNA sequence. It resulted to be 361 bp long, containing 2 introns of 72 and 73 bp respectively. The in silico translation of Hytlo1 genomic DNA sequence corresponded to that of the cDNA.

2. Expression Analysis of Hytlo1 Gene

Northern analysis indicated that the transcription of the *T. longibrachiatum* Hytlo1 gene was strongly activated when *T. longibrachiatum* was grown in a basic salt medium (SMS) in the presence of sucrose, cellulose and chitin, and less in the presence of tomato leaf extracts, or *R. solani* culture filtrate or cell walls (FIG. 1).

3. Purification of the HYTLO1 Protein

One hundred microliter of a *T. longibrachiatum* MK1 spore suspension $10^8$/ml was used to inoculate Erlenmeyer flasks containing 100 ml of Murashige and Skoog (M&S base medium) enriched with 1% sucrose. After 7 days of growth at 25° C. and 150 rpm (revolution per minute) the culture filtrate (CF) was separated from the biomass by filtration with Miracloth paper (Calbiochem La Jolla, Calif., USA) and subsequently centrifugated at 20.000 rpm for 20 min. The obtained clear CF was poured in a separator funnel, vigorously shaken for 5 minutes and decanted for 5 more minutes. At this point, two different phases appeared, a clear liquid and a consistent foam on the surface. The latter was recovered and dissolved in 70% ethanol. It contains the purified protein. Protein concentration was determined by a Bradford Dc protein assay (Bio-Rad, Richmond, Calif., USA) or by Qubit protein kit assay (Invitrogen) and samples were stored at −20° C. until use. This protocol produces about 1.5 mg of pure HYTLO1 from 100 ml of culture filtrate. Aliquots of the protein were run on a SDS-PAGE and silver stained to confirm the purification (FIG. 2).

4. HYTLO1 has a Direct Inhibitory Effect on Plant Pathogens.

Purified HYTLO1 had direct inhibitory effect on germination of spores of *Botrytis cinerea* and *Alternaria* spp., but not of *T. harzianum* as shown in FIG. 3. Antifungal effect of *T. longibrachiatum* HYTLO1 was also tested in comparison with similar hydrophobins (of similar size) from two different *Trichoderma* strains, but only HYTLO1 from *T. longibrachiatum* strain MK1 exhibited a strong antifungal effect on a ELISA-based inhibition assay (FIG. 4).

5. HYTLO1 Beneficially Affects on Plants.

5a—HYTLO1 Activates Systemically Different Plant Defense Responses

In order to verify if HYTLO1 treatments induce a per se stimulation of plant defence reactions we first applied by leaf injection purified HYTLO1 on tomato, and observed under UV light the accumulation of fluorescent compounds as a typical activation of defense responses (FIG. 5). We analyzed the plant biochemical reaction to HYTLO1, which resulted stimulatory for the formation of the superoxide anion and hydrogen peroxide, for anion superoxide dismutase (SOD) and LOX activity, and the accumulation of the phytoalexin rishitin (FIG. 6). These responses have also been found in leaves distant from the site of application, thus demonstrating a systemic effect. In addition, we found that the same treatment of tomato leaves with purified HYTLO1 induced the activation of at least 3 different defense-related genes encoding for PR (Pathogenesis-Related) protein PR1, PR2 and PIN1, typically induced by salicylic acid and jasmonic acid, as demonstrated by a RT-PCR amplification of the relevant RNAs (FIG. 7).

5b. HYTLO1 Protect Plants from Pathogen Infection

Figure 8:
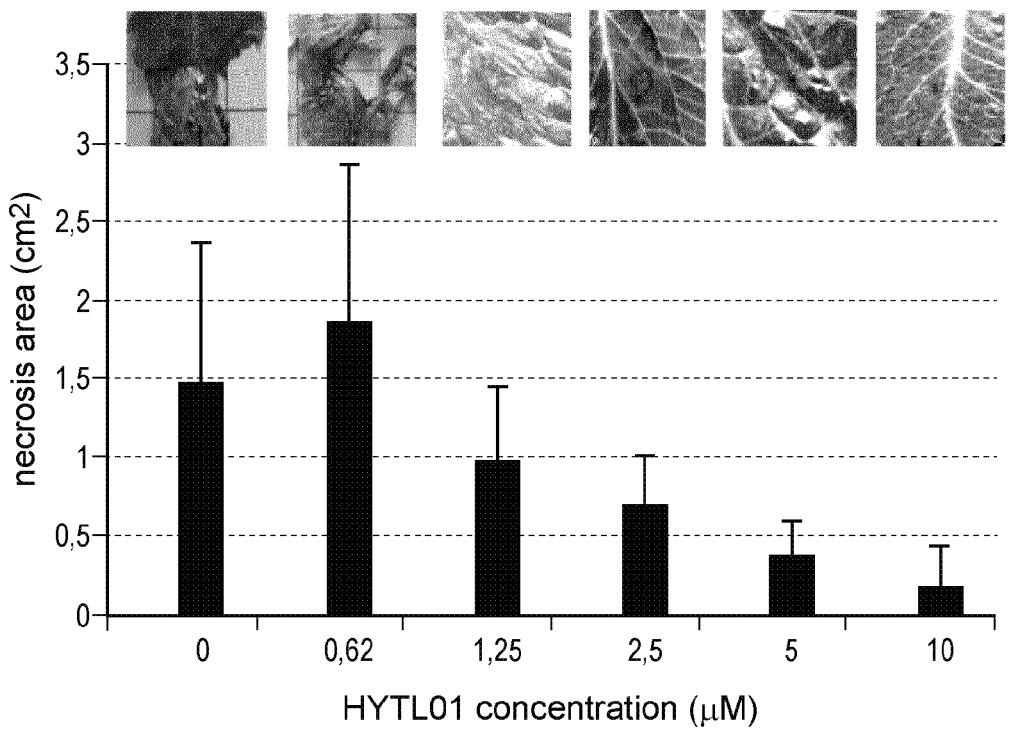

In order to determine if purified HYTLO1 is able to protect the plant from foliar infection by a pathogenic fungus, the protein was tested on tomato grown-up plants against *Botrytis cinerea*. Indeed the application of any tested concentration of HYTLO1 above 1.25 μM (concentration of the HYTLO1 solution of which 10 μL were applied) significantly reduced the size of the developing necrotic area caused by the pathogen up to 72 hr after the inoculation (FIG. 8). This demonstrate that HYTLO1 can be used directly as an antimicrobial agent for plant protection.

5c. HYTLO1 Enhances Plant Growth and Development.

Figure 9:
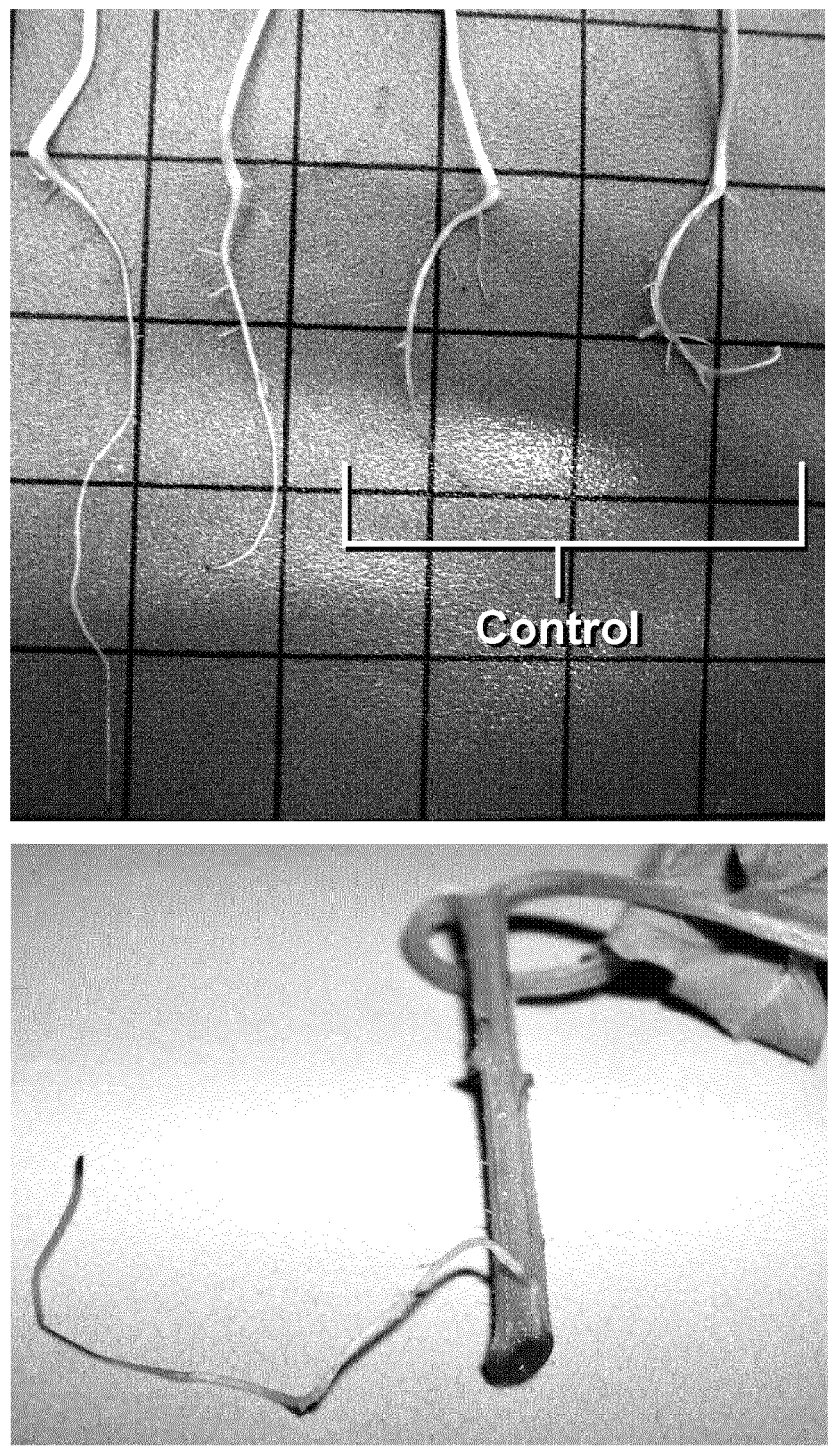
Figure 10:
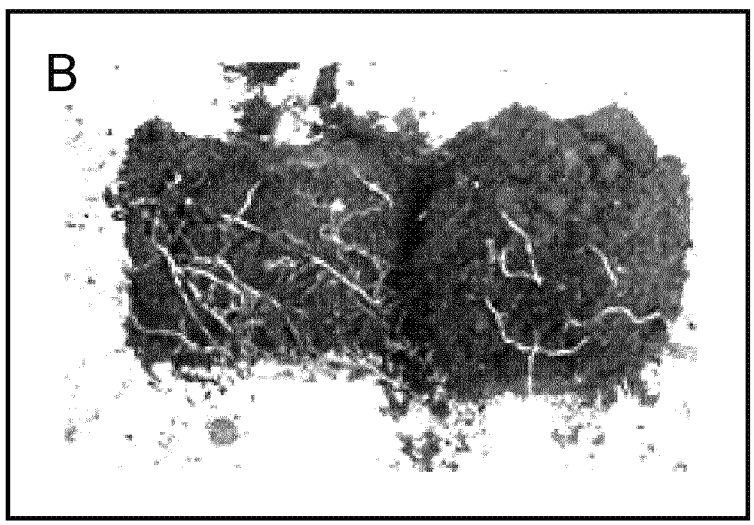
Figure 10:
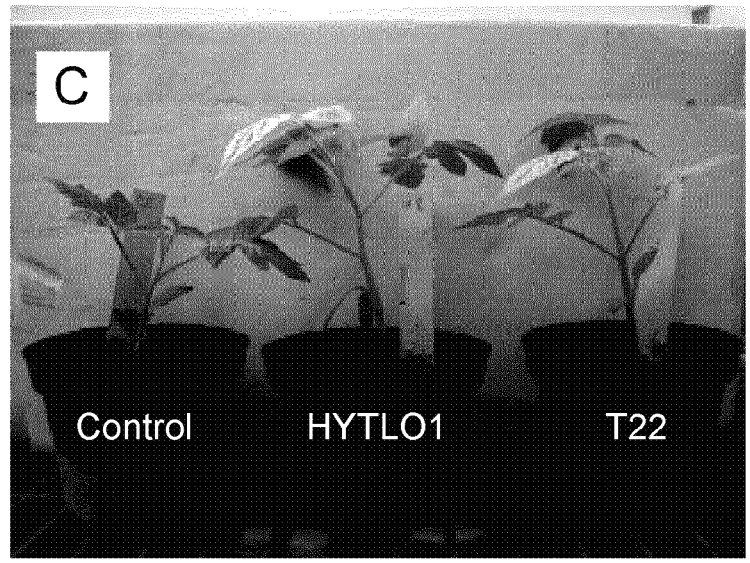
Figure 10:
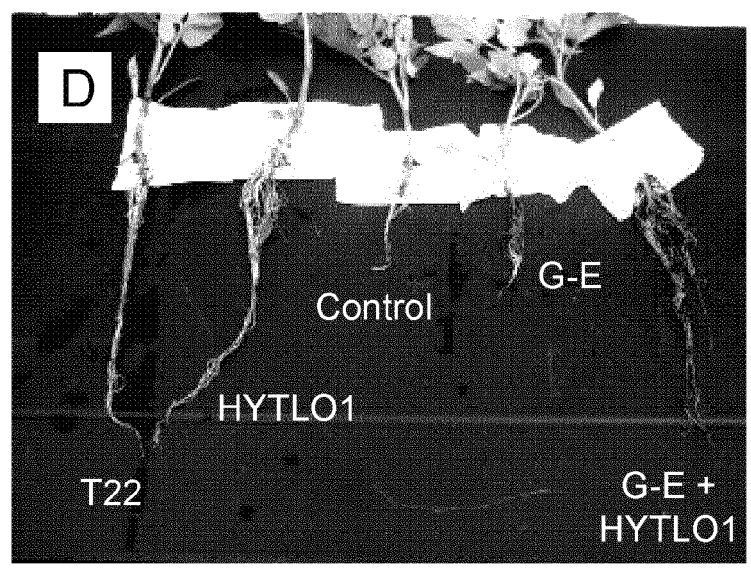

In order to investigate the effect of HYTLO1 on the development of plants, either at the level of seed germination, germling formation and survival, root formation, stem elongation and thickness, foliar development, as well as general plant size, various experiments were performed with the purified protein. Assays made on cuttings demonstrated that HYTLO1 at concentrations as low as 0.31 μM promoted root growth and development (FIG. 9). The protein clearly stimulated rhizogenesis on different plants. For instance, tomato seeds germinated in the presence of HYTLO1 applied at concentrations from $10^{-6}$ to $10^{-9}$ M resulted in plantlets with a root apparatus more than double of the untreated control (data not shown), while tomato cuttings dipped in solutions containing HYTLO1 0.075 and 0.018 μM, formed de novo roots after 15 days (no root formation was observed in controls) (FIG. 9). Experiments on plants were performed in vivo by watering and spraying tomato plants with a HYTLO1 0.01 μM solution as described in the legend of FIG. 10. In these experiments, the effect of HYTLO1 was also compared with that of the commercial biocontrol strain *T. harzianum* T22 (applied as spore suspension according the typical application rate of commercial products) and that of the germinating hormone 1-naphthaleneacetic acid (GERMON E—produced by L. Gobbi, Italy) (applied at the typical application rate of commercial products). Applications were made once per week for one month by watering the tomato plants. Results, expressed in terms of plant height and length, root length and weight, number of leaves, stem diameter and weight, are combined and shown in FIG. 10 and FIG. 11. HYTLO1 treatment increased all of the growth parameters considered in comparison to any of the other treatments as well as of the untreated control. The growth promotion effect of HYTLO1 apart from tomato (Solanaceae) was also confirmed on representative plant species of other plant families (FIG. 12) shows as examples the effect on *Arabidopsis thaliana* (Brassicaceae), *Cucumis sativus* (Cucurbitaceae), and *Lotus japonicus* (Leguminosae)). The experiments demonstrate that HYTLO1 can be effectively used to promote growth and productivity of a variety of crop plants, as well to stimulate seed germination, and root formation.

6. Transgenic Expression of the Hytlo1 Gene Improves Root Growth and Disease Resistance We obtained several tomato plant lines expressing Hytlo1 by using either a *Agrobacterium tumefaciens* transient assay (ATA) method or a PVX-mediated transformation (PVX::HYTLO1). A few lines were selected based on a positive Hytlo1 expression, as detected by Dot-Blotting and RT-PCT and tested an improved ability to form roots as well as for resistance to *B. cinerea* infection. When cuttings of the selected transgenic tomato plants were dipped in water, they quickly formed many de novo roots already after 12 days (no roots formed in the controls) (FIG. 13). When tested for disease resistance (*B. cinerea*), all of three selected lines allowed the formation of significantly smaller necrotic lesion in comparison to the untransformed and empty-vector transformed controls (or the control transformed with a PVX::GFP construct) (FIG. 14). These experiments further confirmed the anti-pathogen and plant growth promotion activity of HYTLO1, and indicate that the Hytlo1 gene can be used transgenically to enhance crop agronomical performance.

7. HYTLO1 has a Key Role of in the Biocontrol Activity of *T. longibrachiatum*

The role of HYTLO1 on the biocontrol and plant growth promotion effect of *Trichoderma longibrachiatum* was demonstrated by targeted knock-out of the Hytlo1 gene by using a standard protoplast transformation method based on treatment with polyethylene glycol (PEG) was used (Punt et al., 1987, Gene, 56:117-124). The lack of Hytlo1 transcripts in a few randomly selected mutants was confirmed by RT-PCR and Northern analysis. The growth rate of the selected Δ-Hytlo1 mutants was the same as of wild type both on solid or liquid growth substrates, while spores were similar in colour, shape and number to those of the wild type. However, the selected mutants were strongly impaired when growing against *R. solani* or *P. ultimum* in vitro (data not shown), and showed a clearly reduced in vivo biocontrol activity (FIG. 15). Further, the negative effect of the Hytlo1 targeted knock-out on the plant growth promotion ability of the wild type *T. longibrachiatum* strain MK1 was also demonstrated in vivo (FIG. 16) both in terms of plant weight and root length enhancement. These experiments clearly demonstrate that HYTLO1 has a key role in the positive interaction between *Trichoderma longibrachiatum* and plants, and further confirms the beneficial properties of this protein.

8. HYTLO1 Enhances the Beneficial Effect of Fungal Secondary Metabolites

In order to further demonstrate the usefulness of HYTLO1 for plant growth promotion applied either singly or in combination with other beneficial molecules, we tested the combined effect of the protein with secondary metabolites produced by different species of fungi, including *Trichoderma* spp. Tested metabolites include 6PP and Harzianic Acid, and experiments were performed on seed germination, stem or root elongation as well fresh/dry weight. The results shown in Table 1 were obtained by using cucumber seeds coated with the solutions of the tested compounds, that were then transferred in Petri dishes and left to germinate on filter humid paper. First seed germination was evaluated, then the germinated seedlings were transplanted into pots containing sterilised soil. Other two treatments with the purified molecules were performed at 10 days interval, by drenching the soil with the solutions at the final concentrations of $10^{-7}$M for 6PP and HA, and $10^{-8}$M for HYTLO1. In two-compounds application, half dose of each molecule was used. In three-compound applications, one third of the dose of each molecules was used. Each treatments consisted of 8 plants. Results were collected 30 days after seed coating. Control was produced by adding water instead of the molecule solutions. The effect of the minimal amounts of solvents eventually contained in HA and 6PP solution was preliminary tested, with no differences observed in comparison to water control. The results shown in Table 1 that all of the three tested molecules have a significant beneficial effect on seed germination and plant growth, and that they can be synergistically combined for enhanced effectiveness. The occurrence of synergism was demonstrated for the values underlined in Table 1 by using the Limpel's formula, also as modified by Lorito et al., (Lorito M., et al. 1994. Microbiology UK, 140:623-629).

TABLE 1

Effect of combined application of HYTLO1, HA and 6PP on cucumber seed germination and growth promotion.

| Treatments | Seed germination (24 h) SD +− 9% | plant height (cm) SD +− 2.5 cm | Root length (cm) SD +− 2.1 cm | Plant fresh weight (g) SD +− 2.5 g | Plant dry weight (g) SD +− 1.3 g |
|---|---|---|---|---|---|
| HYTLO1 | 78% | 24.9 | 14.6 | 24.76 | 8.4 |
| increase % vs. Control | +30% | | 17.1 | 34.1 | 51.2 |
| 6PP | 75% | 21.8 | 17.6 | 22.04 | 7.1 |
| increase % vs. Control | +25% | | 31.1 | 25.9 | 42.3 |
| HA | 75% | 27.4 | 13.6 | 23.36 | 7.6 |
| increase % vs. Control | +25% | 8.4 | 10.7 | 30.1 | 46.1 |
| HYTLO1 + 6PP | 64% | 24.1 | 14.1 | 23.09 | 7.9 |
| increase % vs. Control | +6% | | 14.2 | 29.3 | 48.1 |
| HYTLO1 + HA | 64% | 23.8 | 18.3 | 20.98 | 6.8 |
| increase % vs. Control | +6% | | 33.6 | 22.2 | 39.7 |
| HYTLO1 + HA + 6PP | 54% | 28.6 | 12.4 | 23.53 | 8.0 |
| increase % vs. Control | | 12.2 | | 30.6 | 48.8 |

9. HYTLO1 Enhances the Beneficial Effect of Biocontrol Agents *Trichoderma* Spp.

In order to demonstrate the usefulness of HYTLO1 to enhance the beneficial effect of different *Trichoderma* strains commercially applied for biocontrol, the purified protein was applied in combination with two strains of *T. harzianum* (T22 and TH1) and one strain of *T. asperellum* (CS1). The results are shown in Table 2 and expressed in terms of increased stem and root length or fresh/dry weight. Cucumber seeds were coated with the purified molecule solutions and/or spore suspension, transferred into Petri dishes and left to germinate on humid filter paper. Germinated seedlings were transplanted into pots containing sterilised soil. Other two treatments with the purified molecules were performed at 7 days interval, by drenching the soil with the solutions at the final concentrations of $10^{-8}$M for HYTLO1, and 1 ml of a $10^7$ spore/ml suspension per 10 ml soil. In two-compounds application, half dose of each molecule was used. Each treatments was performer on at least 8 plants, and results were collected 20 days after seed coating. This experiment confirmed the beneficial effect exerted by HYTLO1 alone and in combination with *Trichoderma* species on plant growth. The experiment demonstrates that the presence of HYTLO1 improves the effect of living *Trichoderma* preparations made of different active principles. In particular, and only as an example, combined treatment with *T. harzianum* T22+HYTLO1, and *T. harzianum* strain TH1+HYTLO1 determined a significant increase in plant growth promotion effect of up to 33% more compared to controls (synergistic results as by the Limpel's formula are underlined in the Table).

TABLE 2

Effect of combined application of HYTLO1, HA and 6PP and different *Trichoderma* spp. strains on cucumber seed germination and growth promotion. Values are percentage increase compared to water control.

| Treatment | plant height (cm) SD +− 1.5 | Root length (cm) SD +− 2.0 | Plant fresh weight (g) SD +− 2.8 | Plant dry weight (g) SD +− 3.1 |
|---|---|---|---|---|
| HYTLO1 | 1.8 | 8.5 | 4.2 | 7.3 |
| TH1 | 9.5 | 3.5 | 1.4 | 9.1 |
| T22 | 4.8 | 7.8 | 18.6 | 13.3 |
| CS1 | 1.8 | 9.6 | 2.1 | 7.3 |
| TH1 + HYTLO1 | 7.1 | 23.4 | 30.0 | 1.8 |
| T22 + HYTLO1 | 14.3 | 5.5 | 30.7 | 16.4 |
| CS1 + HYTLO1 | 8.9 | 19.1 | 6.3 | 5.5 |

10. HYTLO1 Enhances the Beneficial Effect of *Rhizobium* on Leguminosae Plants.

In order to test the effect of HYTLO1, as well as of the secondary metabolites HA and 6PP on the growth promotion activity of *Rhizobia*, such as *Rhizobium* sp., on legumimosae plants, we used a standard *Rhizobium lotii* on *Lotus japonicus* in vitro system (Barbulova et al., 2005, Functional Plant Biology, 32:529-536). Plant growth and nodule density on the roots were scored four weeks after seeding by comparing untreated controls and the various treatments. Results shown in FIG. 17 and FIG. 18 demonstrate that HYTLO1, either applied alone or in combination with HA or 6PP enhances the plant growth promotion effect of *Rhizobia*, such as *Rhizobium* sp., on plant, and that this phenomenon may be due to an increased number of nodule formation on the treated roots. This data demonstrate that HYTLO1 can be used to enhance the efficacy and usefulness of *Rhizobia*-based, such as *Rhizobium*-based, microbial inocula, in terms of promotion of plant agronomic performance as well as in fertilizing the soil due to nitrogen fixation by the nodulated bacteria.

The invention claimed is:

1. A method for improving root development in a Leguminosae plant, the method comprising:
applying to the Leguminosae plant a composition comprising a protein having at least 90% sequence similarity with the amino acid sequence of SEQ ID NO: 1 or a nucleic acid comprising sequence encoding a protein having at least 90% sequence similarity with the amino acid sequence of SEQ ID NO:1, wherein the composition comprising the protein or the nucleic acid results in improved root development.

2. The method according to claim 1, wherein the composition further comprises a carrier.

3. The method according to claim 1, wherein the composition further comprises a plant biostimulant.

4. The method according to claim 3, wherein the plant biostimulant is selected from the group consisting of (i) a Trichoderma species, (ii) harzianic acid, (iii) 6-pentyl-a-pyrone, (iv) Rhizobia; and combinations thereof.

5. The method according to claim 1, wherein the composition comprises biomass of a Trichoderma longibrachiatum strain.

6. The method according to claim 1, wherein the improved root development comprises improved root nodulation.

7. A seed of a Leguminosae plant treated with a composition comprising a carrier and a protein having at least 90% sequence similarity with the amino acid sequence of SEQ ID NO: 1 or a nucleic acid comprising a sequence encoding a protein having at least 90% sequence similarity with the amino acid sequence of SEQ ID NO: 1, wherein the seed produces a plant having improved root development.

8. The seed according to claim 7, wherein the composition further comprises a plant biostimulant.

9. The seed according to claim 7, wherein the plant biostimulant is selected from the group consisting of (i) a Trichoderma species, (ii) harzianic acid, (iii) 6-pentyl-a-pyrone, (iv) Rhizobia; and combinations thereof.

10. The seed according to claim 7, wherein the composition comprises biomass of a Trichoderma longibrachiatum strain.

11. A transgenic Leguminosae plant comprising a nucleic acid sequence coding for a protein having at least 90% sequence similarity with the amino acid sequence of SEQ ID NO: 1.

12. The transgenic plant according to claim 11, wherein the transgenic plant exhibits improved root development.

13. The transgenic plant according to claim 12, wherein the improved root development comprises improved root nodulation.

14. A-seed transgenic seed of a transgenic plant according to claim 11.

15. The method of claim 1, wherein the applying the nucleic acid comprises introducing into the cells of the Leguminosae plant the nucleic acid encoding a protein having at least 90% sequence similarity with the amino acid sequence of SEQ ID NO: 1.

16. The seed of claim 7, wherein the Leguminosae plant is transfected with the nucleic acid encoding a protein having at least 90% sequence similarity with the amino acid sequence of SEQ ID NO: 1.

* * * * *

SEQUENCE LISTING

<160> NUMBER OF SEQ ID NOS: 5

<210> SEQ ID NO 1
<211> LENGTH: 71
<212> TYPE: PRT
<213> ORGANISM: Trichoderma longibrachiatum strain MK1-KV966 (CBS 137023)

<400> SEQUENCE: 1

```
Ala Val Cys Pro Thr Gly Leu Phe Ser Asn Pro Leu Cys Cys Ser Thr
 1               5                  10                  15

Asn Val Leu Asp Leu Val Gly Val Asp Cys Val Thr Pro Thr Ala Ala
            20                  25                  30

Val Pro Asp Gly Val Phe Phe Gln Ala His Cys Ala Ser Lys Gly Lys
        35                  40                  45

Gln Pro Leu Cys Cys Val Ala Pro Val Ala Lys Gln Gly Val Leu Cys
    50                  55                  60

Gln Lys Pro Ile Gly Thr Gln
65                  70
```

<210> SEQ ID NO 2
<211> LENGTH: 445
<212> TYPE: DNA
<213> ORGANISM: Trichoderma longibrachiatum strain MK1-KV966 (CBS 137023)

<400> SEQUENCE: 2

```
gctgtctgcc ctaccggcct cttctccaac ccgctctgct gctccaccaa cgtcctcgac      60
ctcgtcggcg ttgactgcgt cacccccacc gccgctgtcc ccgatggcgt cttcttccag     120
gcccactgcg cctccaaggg caagcagccc tctgctgtg ttgctcccgt tgccaagcag      180
ggtgttctgt gccagaagcc catcggcacc cagtaaagca acggtttgct ttaccggcgg     240
cagtcttgag ttgccctcgg gcctcacaga ctggcatata tcattttggg ctcgcaaatg     300
ggaggatttt gaggggtttg aaggcctggg tttggcctag ttggaggggg aggattgggt     360
aatggcagct ttgcgaccag gacatagatg ttgatagagt gtgtagtcaa tacatatcag     420
aaaagttgga gaaaaaaaaa aaaaa                                           445
```

<210> SEQ ID NO 3
<211> LENGTH: 19
<212> TYPE: DNA
<213> ORGANISM: Artificial sequence
<220> FEATURE:
<223> OTHER INFORMATION: Designed primer

<400> SEQUENCE: 3

```
gctgtctgcc ctaccggcc                                                   19
```

<210> SEQ ID NO 4
<211> LENGTH: 18
<212> TYPE: DNA
<213> ORGANISM: Artificial sequence
<220> FEATURE:
<223> OTHER INFORMATION: Designed primer

<400> SEQUENCE: 4

```
ttactgggtg ccgagggc                                                    18
```

<210> SEQ ID NO 5
<211> LENGTH: 114
<212> TYPE: PRT

```
<213> ORGANISM: Artificial Sequence
<220> FEATURE:
<223> OTHER INFORMATION: hydrophobin motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: MISC_FEATURE
<222> LOCATION: (8)..(12)
<223> OTHER INFORMATION: Xaa can be any naturally occurring amino acid
      and may be present or absent
<220> FEATURE:
<221> NAME/KEY: misc_feature
<222> LOCATION: (15)..(25)
<223> OTHER INFORMATION: Xaa can be any naturally occurring amino acid
<220> FEATURE:
<221> NAME/KEY: MISC_FEATURE
<222> LOCATION: (26)..(58)
<223> OTHER INFORMATION: Xaa can be any naturally occurring amino acid
      and may be present or absent
<220> FEATURE:
<221> NAME/KEY: misc_feature
<222> LOCATION: (60)..(67)
<223> OTHER INFORMATION: Xaa can be any naturally occurring amino acid
<220> FEATURE:
<221> NAME/KEY: MISC_FEATURE
<222> LOCATION: (68)..(82)
<223> OTHER INFORMATION: Xaa can be any naturally occurring amino acid
      and may be present or absent
<220> FEATURE:
<221> NAME/KEY: misc_feature
<222> LOCATION: (84)..(88)
<223> OTHER INFORMATION: Xaa can be any naturally occurring amino acid
<220> FEATURE:
<221> NAME/KEY: MISC_FEATURE
<222> LOCATION: (89)..(92)
<223> OTHER INFORMATION: Xaa can be any naturally occurring amino acid
      and may be present or absent
<220> FEATURE:
<221> NAME/KEY: misc_feature
<222> LOCATION: (95)..(100)
<223> OTHER INFORMATION: Xaa can be any naturally occurring amino acid
<220> FEATURE:
<221> NAME/KEY: MISC_FEATURE
<222> LOCATION: (101)..(112)
<223> OTHER INFORMATION: Xaa can be any naturally occurring amino acid
      and may be present or absent
<220> FEATURE:
<221> NAME/KEY: misc_feature
<222> LOCATION: (114)..(114)
<223> OTHER INFORMATION: Xaa can be any naturally occurring amino acid

<400> SEQUENCE: 5

Xaa Cys Xaa Xaa Xaa Xaa Xaa Xaa Xaa Xaa Xaa Xaa Cys Cys Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Cys Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80
```

-continued

```
Xaa Xaa Cys Xaa Xaa Xaa Xaa Xaa Xaa Xaa Xaa Cys Cys Xaa Xaa
            85                  90                  95

Xaa Xaa Xaa Xaa Xaa Xaa Xaa Xaa Xaa Xaa Xaa Xaa Xaa Xaa Xaa
            100                 105                 110

Cys Xaa
```